United States Patent
Marton et al.

(10) Patent No.: US 11,364,243 B2
(45) Date of Patent: Jun. 21, 2022

(54) METHODS FOR TREATING CANCER WITH A WEE1 INHIBITOR

(71) Applicant: Merck Sharp & Dohme Corp., Rahway, NJ (US)

(72) Inventors: Matthew J. Marton, Whitehouse Station, NJ (US); Yair Benita, Tel Aviv (IL)

(73) Assignee: MERCK SHARP & DOHME CORP., Rahway, NJ (US)

(*) Notice: Subject to any disclaimer, the term of this patent is extended or adjusted under 35 U.S.C. 154(b) by 13 days.

(21) Appl. No.: 16/705,592

(22) Filed: Dec. 6, 2019

(65) Prior Publication Data

US 2020/0171035 A1 Jun. 4, 2020

Related U.S. Application Data

(63) Continuation of application No. 15/314,650, filed as application No. PCT/US2015/032351 on May 26, 2015, now abandoned.

(60) Provisional application No. 62/004,298, filed on May 29, 2014.

(51) Int. Cl.
| | |
|---|---|
| *C12Q 1/6886* | (2018.01) |
| *A61K 31/00* | (2006.01) |
| *A61P 35/00* | (2006.01) |
| *A61K 31/519* | (2006.01) |
| *A61K 31/555* | (2006.01) |
| *A61K 31/513* | (2006.01) |
| *A61K 31/704* | (2006.01) |
| *A61K 45/06* | (2006.01) |
| *A61K 31/7048* | (2006.01) |
| *A61K 31/4745* | (2006.01) |
| *A61K 31/4188* | (2006.01) |
| *A61K 31/7068* | (2006.01) |
| *A61K 31/407* | (2006.01) |
| *A61K 31/337* | (2006.01) |

(52) U.S. Cl.
CPC .......... *A61K 31/519* (2013.01); *A61K 31/337* (2013.01); *A61K 31/407* (2013.01); *A61K 31/4188* (2013.01); *A61K 31/4745* (2013.01); *A61K 31/513* (2013.01); *A61K 31/555* (2013.01); *A61K 31/704* (2013.01); *A61K 31/7048* (2013.01); *A61K 31/7068* (2013.01); *A61K 45/06* (2013.01); *C12Q 1/6886* (2013.01); *C12Q 2600/106* (2013.01); *C12Q 2600/156* (2013.01); *C12Q 2600/158* (2013.01)

(58) Field of Classification Search
CPC ............ C12Q 1/6886; C12Q 2600/106; C12Q 2600/112; C12Q 2600/118; C12Q 2600/156; C12Q 2600/158; A61K 31/00; A61P 35/00

See application file for complete search history.

(56) References Cited

PUBLICATIONS

Mir et al., "In silico analysis of kinase expression identifies WEE1 as a gatekeeper against mitotic catastrophe in glioblastoma," Cancer Cell. 18(3):244-57. PMID: 20832752. (Year: 2010).*

* cited by examiner

*Primary Examiner* — Theodore R. Howell
(74) *Attorney, Agent, or Firm* — Mintz, Levin, Cohn, Ferris, Glovsky and Popeo, P.C.

(57) ABSTRACT

The present invention relates generally to the use of gene mutations, whose presence or absence are useful for predicting a patient's response to treatment with an antiproliferative agent, in particular a WEE1 inhibitor. The presence or absence of a mutation to the TP53 gene, can be used to predict response to treatment with a WEE1 inhibitor in a patient presenting with a cancerous condition.

16 Claims, 1 Drawing Sheet

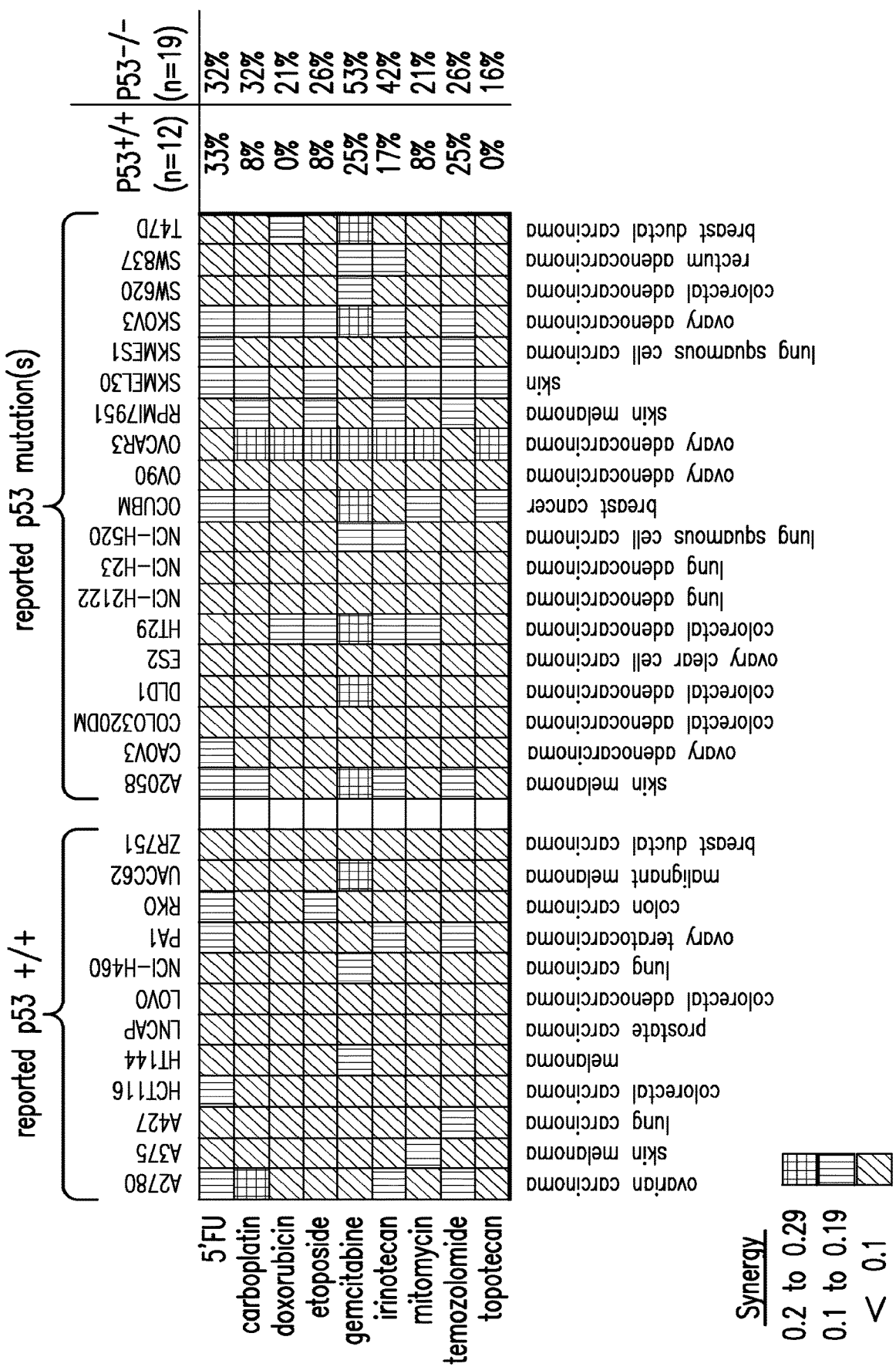

METHODS FOR TREATING CANCER WITH A WEE1 INHIBITOR

FIELD OF THE INVENTION

The present invention relates generally to the use of gene mutations, whose presence or absence are useful for predicting a patient's response to treatment with an antiproliferative agent, in particular a WEE1 inhibitor. The presence or absence of a mutation to the TP53 gene, can be used to predict response to treatment with a WEE1 inhibitor in a patient presenting with a cancerous condition.

BACKGROUND OF THE INVENTION

Many commonly used anti-cancer drugs indiscriminately target DNA in dividing cells and ultimately cause DNA damage. This, in turn, triggers activation of cell cycle checkpoints which arrest progression of the cell cycle (at the G1, S, or G2/M phases) with the purpose of allowing time for the DNA to be repaired before the cell undergoes DNA replication or division. From a therapeutic standpoint, inhibition of checkpoint kinases that mediate cell cycle arrest could force tumor cells to continue cell division before chemically-induced DNA damage is repaired, eventually causing apoptosis or mitotic catastrophe (Medema, R. H. and Macurek, L., Oncogene, 2012, 31(21): 2601-2613). Cell line studies support this hypothesis and show chemosensitization and radiosensitization by pharmacologic or genetic disruption of checkpoint kinase activity including CHK1, WEE1, ATR, and ATM. Inhibitors against these kinases are at various stages of preclinical and clinical development for their ability to sensitize tumor cells to therapeutic DNA damage.

The checkpoint kinase WEE1 catalyzes an inhibitory phosphorylation of both CDK1 (CDC2) and CDK2 on tyrosine 15 (Parker, L. L. and Piwnica-Worms, H., Science, 1992, 257(5078): 1955-1957; Watanabe, N., et al., Embo J., 1995, 14(9): 1878-1891). WEE1-dependent inhibition of CDK1 and CDK2 arrests the cell cycle in response to extrinsically induced DNA damage (Hamer, P. C. D., et al., Clin. Cancer Res., 2011, 17(13): 4200-4207). WEE1 activity is also essential for the unperturbed cell cycle (Mcgowan, C. H. and Russell, P., Embo J., 1993, 12(1): 75-85; Tominaga, Y., et al., Intl. J. Biol. Sci., 2006, 2(4): 161-170). Cell synchronization studies in normal human fibroblasts revealed that similar amounts of WEE1 protein were detected in both S and G2/M phases, but that its greatest activity was in S phase of the cell cycle (Watanabe, N., 1995). Further, upon conditional WEE1 knockout in mouse embryonic fibroblasts (MEFs), cells show evidence of genomic instability, malfunctioning checkpoints, and premature mitosis (Tominaga, et al., 2006). This phenotype was explained in part by recent findings that demonstrate a critical role for WEE1 in DNA synthesis. Knockdown of WEE1, in the absence of DNA damaging agents, led to rapid and robust detection of DNA double strand breaks specifically in S-phase cells undergoing DNA replication (Beck, H., et al., J. Cell Biol., 2010, 188(5): 629-638; Dominguez-Kelly, R., et al., J. Cell Biol., 2011, 194(4): 567-579). Data support a model of WEE1-dependent genomic stability in which WEE1 knockdown or inhibition leads to aberrantly high activity of CDK 1 and 2, resulting in inappropriately timed firing of excessive DNA replication origins that quickly depletes nucleotide pools and leads to stalled replication forks which, in the absence of WEE1 activity, are substrates for DNA exonucleases and resolve into DNA doubles strand breaks (Beck, H., et al., 2012).

Deregulated WEE1 expression or activity is believed to be a hallmark of pathology in several types of cancer. WEE1 is often overexpressed in glioblastomas and its activity protects this tumor type from mitotic catastrophe such that high WEE1 levels are associated with poor prognosis (Mir, S. E., et al., Cancer Cell, 2010, 18(3): 244-257). High expression of WEE1 was found in malignant melanoma and correlated with poor disease-free survival in this population (Magnussen, G. I., et al., Plos One, 2012, 7(6)). Aberrant WEE1 expression has been implicated in additional tumor types such as hepatocellular carcinoma (Masaki, T., et al., Hepatology, 2003, 37(3): 534-543), breast cancer (Iorns, E., et al., Plos One, 2009, 4(4)), colon carcinoma (Backert, S., et al., Intl., J. Cancer, 1999, 82(6): 868-874)), lung carcinoma (Yoshida, T., et al., Annals of Oncology, 2004, 15(2): 252-256) and head and neck squamous cell carcinoma (Wu, Z. X., et al., Mol. & Cell. Proteomics, 2011, 10(12)). Advanced tumors with an increased level of genomic instability may require functional checkpoints to allow for repair of such lethal DNA damage. As such, WEE1 represents an attractive target in advanced tumors where its inhibition is believed to result in irreparable DNA damage (Sorensen, C. S. and Syljuasen, R. G., Nuc. Acids Res., 2012, 40(2): 477-486).

The TP53 gene, which encodes the p53 protein, is an important regulator of the cell-cycle as a key regulator of the $G_1$ checkpoints and is one of the most frequently mutated genes in cancer (Molinari, M., Cell. Prolif., 2000, 33: 261-174). Cells lacking the $G_1$ checkpoint are predicted to be more dependent on the WEE1-mediated S or G2 checkpoint. Thus, p53-deficient tumors treated with $G_2$ checkpoint abrogators may be particularly susceptible to DNA damage (Kawabe, T., Mol. Cancer Ther., 2004, 3: 513-519; Bucher, N., and Britten, C. D., Br. J. Cancer, 2008, 98: 523-528).

There is a need for biomarkers that can be used to predict which patients are amenable to treatment with specific therapies, particularly for patients who are non-responsive or who are likely to become refractive to first line therapies. It is, therefore, an object of this invention to provide biomarkers to select patients likely to respond to treatment with a WEE1 inhibitor.

SUMMARY OF THE INVENTION

The instant invention relates generally to the identification of TP53 gene mutations whose presence or absence are useful for evaluating and classifying patients for treatment with a WEE1 inhibitor. In one embodiment of the invention, the TP53 gene mutations resulting in loss of function are used to identify patients likely to respond to treatment with a WEE1 inhibitor. In another embodiment, the invention is a method for treating a patient diagnosed with a WEE1 associated cancer with a WEE1 inhibitor, wherein the cancer cells of said patient are characterized by the presence of a mutation in TP53 which renders p53 non-functional. In still another embodiment, the invention is a method for treating a cancer patient who is responsive or predicted to be responsive to treatment with a WEE1 inhibitor, wherein the cancer cells of said patient are characterized by the presence of a mutation in TP53 which renders p53 non-functional.

BRIEF DESCRIPTION OF THE DRAWINGS

FIG. 1: Effect of TP53 mutation status on the degree of synergy observed between WEE1-1 and various DNA-damaging agents.

DETAILED DESCRIPTION OF THE INVENTION

Many anti-cancer treatments act by damaging DNA, which subsequently initiates the DNA damage response (DDR) and activates checkpoint kinases to arrest division while the DNA is repaired. WEE1, a tyrosine kinase, is activated by the DDR to phosphorylate and inhibit cyclin dependent kinases (CDKs) 1 and 2 and, as such, arrest cell division. Inhibiting WEE1 potentiates DNA damaging treatments by abrogating cell cycle arrest and proper DNA repair.

WEE1-1, also known as 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one, is a potent ($IC_{50}$=5.2 nM) and selective ATP-competitive small molecule inhibitor of WEE1 (Hirai, H., et al., *Mol. Cancer Ther.*, 2009, 8(11): 2992-3000) that is currently under clinical development as an anti-tumor agent in combination with standard of care (SOC) chemotherapeutics (Stathis, A. and Oza A., *Drug News & Perspectives*, 2010, 23(7): 425-429; Schellens, J. H. M., et al., *J. Clin. Oncol.*, 2011, 29: 2011 (suppl; abstr 3068); Mizuarai, S., et al., *Mol. Cancer*, 2009, 8: 34). Previous studies on WEE1-1 have demonstrated its potential as an adjunct or sensitizer to currently used standard of care (SOC) chemotherapeutics by its ability to force unscheduled mitosis that ultimately results in apoptosis or mitotic catastrophe (Hirai, H., et al., *Cancer Biol. & Ther.*, 2010, 9(7): 514-522; Aarts, M., et al., *Cancer Discovery*, 2012, 2(6): 524-539; Indovina, P. and Giordano A., *Cancer Biol. & Ther.*, 2010, 9(7); 523-525; Wang, Y. L., et al., *Cancer Biol. & Ther.*, 2004, 3(3): 305-313). However, the potential therapeutic effect of WEE1 inhibition in the absence of SOC chemotherapy is less defined. RNAi knockdown of WEE1 inhibited proliferation of cancer cell lines (Iorns, E., et al., *Cancer Targets*, 2009, Plos One, 4(4); Murrow, L. M., et al., *Breast Cancer Research and Treatment*, 2010, 122(2): 347-357) and recently it was demonstrated that WEE1-1 alone can induce apoptosis in sarcoma cell lines treated in vitro (Kreahling, J. M., et al., *Mol. Cancer Ther.*, 2012, 11(1): 174-182).

The p53 protein is encoded by the TP53 gene. Pre-clinical studies have suggested that WEE1-1 may be selectively effective in patients having p53-defective tumors, that is, in patients whose tumors harbor mutations in TP53 which render p53 non-functional. While over 25,000 mutations in the TP53 gene have been reported, not every mutation is expected to lead to a loss of function. Moreover, even as to mutations associated with loss of function, all are not equal in their ability to extinguish the functionality of p53.

Applicants herein have developed a method to identify a subset of loss of function mutations, referred to as a "p53 filter", by assigning to each type of mutation (see Table 1) a point value related to the likelihood that the mutation results in loss of function of p53, and in one embodiment, sensitivity to treatment with a WEE1 inhibitor, such as WEE1-1. As shown in Table 3, the evidence score of each gene mutation was calculated based on adding together the point values for the mutation: stop codon mutation, splice site mutation, dominant negative mutation, p53 signature p value <0.05, mutation reported >10× times in somatic tissue at amino acid level, mutation reported >10× in somatic tissue at nucleotide level. The TP53 mutation score of a patient is calculated by identifying the various gene mutations in Table 3 in the cancer cell of the patient, and adding together the evidence score of each identified gene mutation.

Thus, in one embodiment of the invention, patients whose TP53 mutation score is 2.0, 3.0, 4.0, 5.0, 6.0, 7.0, 8.0, 9.0, 10.0 or greater according to Table 3 are identified as those patients most likely to respond to treatment with a WEE1 inhibitor and are selected for treatment with a WEE1 inhibitor. In another embodiment of the invention, patients treated with a WEE1 inhibitor whose TP53 mutation score is 2.0, 3.0, 4.0, 5.0, 6.0, 7.0, 8.0, 9.0, 10.0 or greater according to Table 3 are identified as patients most likely to continue to respond to treatment and are selected to continue treatment with a WEE1 inhibitor.

The GENBANK accession number of the p53 protein is NM000546. The GENBANK accession number of the p53 gene is X54156.1. The TP53 gene sequence is also available from the IARC database (http://p53.iarc.fr). While different databases may use different nucleotide or amino acid numbering systems, based on the nucleotide and amino acid information in Table 3, one skilled in the art can readily identify the gene mutation and its location in the p53 gene.

The present invention provides a method of treating cancer or modulating WEE1 activity in a patient comprising the step of:
1) selecting a patient diagnosed with cancer that has one or more TP53 gene mutations according to Table 3, at least one basepair insertion or deletion in the TP53 gene that causes a frameshift in encoding the p53 protein resulting in loss of function, or a combination thereof in the cancer cell;
2) administering a therapeutically effective amount of a WEE1 inhibitor and optionally one or more additional anti-cancer agents to the patient.

The present invention also provides a method of treating cancer or modulating WEE1 activity in a patient, in which the patient is diagnosed with cancer and has one or more TP53 gene mutations according to Table 3, at least one basepair insertion or deletion in the TP53 gene that causes a frameshift in encoding the p53 protein resulting in loss of function, or a combination thereof in the cancer cell; comprising the step of administering a therapeutically effective amount of a WEE1 inhibitor and optionally one or more additional anti-cancer agents to the patient.

The present invention further provides a method of treating cancer or modulating WEE1 activity in a patient, comprising the step of administering a therapeutically effective amount of a WEE1 inhibitor and optionally one or more additional anti-cancer agents to the patient, wherein the patient is diagnosed with cancer and has one or more TP53 gene mutations according to Table 3, at least one basepair insertion or deletion in the TP53 gene that causes a frameshift in encoding the p53 protein resulting in loss of function, or a combination thereof in the cancer cell. In one embodiment, the invention provides a WEE1 inhibitor for use in the treatment of cancer or modulating WEE1 activity in a patient, wherein the patient is diagnosed with cancer and has one or more TP53 gene mutations according to Table 3, or at least one basepair insertion or deletion in the TP53 gene that causes a frameshift in encoding the p53 protein resulting in loss of function, or a combination thereof in the cancer cell, and the treatment optionally comprises one or more additional anti-cancer agents.

In one embodiment, the at least one basepair insertion or deletion in the TP53 gene that causes a frameshift in encoding the p53 protein completely eliminates the DNA binding domain of p53.

In one embodiment, the TP53 gene mutation has an evidence score that is equal or greater than 2.5 according to Table 3. In another embodiment, the TP53 gene mutation has an evidence score that is equal or greater than 3 according to Table 3. In another embodiment, the TP53 gene mutation has an evidence score that is equal or greater than 3.5 according to Table 3. In a further embodiment, the TP53 gene mutation has an evidence score that is equal or greater than 4.0 according to Table 3. In yet a further embodiment, the TP53 gene mutation has an evidence score that is equal or greater than 4.5 according to Table 3. In yet another embodiment, the TP53 gene mutation has an evidence score that is equal to 5.0 according to Table 3. In yet another embodiment, the patient has at least one of the TP53 gene mutations resulting in the amino acid change selected from the group consisting of C238F, R248W and R273L according to Table 3, a stop codon at the codon encoding E298 in the p53 protein, or a deletion of a basepair in the codon encoding V157 in the p53 protein.

In another embodiment of the above method, step 1) is selecting a patient diagnosed with cancer that has two or more TP53 gene mutations according to Table 3, or three or more TP53 gene mutations according to Table 3 in the cancer cell.

In one embodiment of the invention, the AmpliChip p53 Assay (Roche Molecular Systems, Inc., Pleasanton, Calif.) is used to identify the TP53 mutation present in the samples from patients diagnosed with a TP53 associated cancer. The AmpliChip p53 test is a microarray-based resequencing test. The test is designed to detect single nucleotide substitutions and 1 bp deletions in the entire coding region and the flanking splice sites of exons 2-11 of the TP53 gene in either formalin-fixed paraffin-embedded tissue (FFPE) or freshly frozen tissue. The AmpliChip p53 test queries for the presence of sequence alterations through comparative analysis of the hybridization pattern of a series of probes to sample DNA and wild-type reference DNA. The highly redundant probe tiling approach is able to detect a significantly lower abundance of TP53 mutations in samples which contain mixtures of normal and tumor tissue without the need for microdissection. See Li et al. *Current Genomics*, 2008, 9, 466-474.

Those skilled in the art would recognize and appreciate that other methods could be employed to identify the gene mutation present, such as Sanger sequencing, massively parallel sequencing (Next-Generation Sequencing), mass spectrometry, or PCR techniques. The inventive method herein is not tied to the method used to identify the specific p53 loss-of-function mutation or the absence of any such mutation.

WEE1 Inhibitors

In an embodiment of the invention, the WEE1 inhibitor for use in the methods of the instant invention is WEE1-1, the structure of which is as shown below.

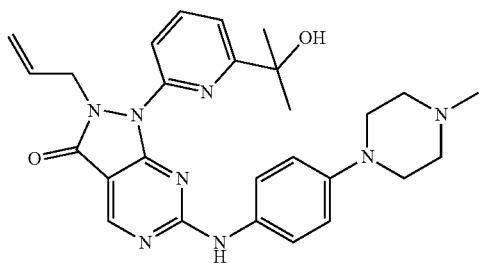

WEE1-1

WEE1-1 is a WEE1 inhibitor which is useful for the treatment of cancer. WEE1-1 is also known as 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one. WEE1-1 has been described in U.S. Pat. No. 7,834,019, and in PCT International Publication WO2007/126122, WO 2007/126128 and WO2008/153207, which are incorporated by reference herein in their entirety. Crystalline forms of WEE1-1 are described in US Publication US2010-0124544 and PCT International Publication WO2011/034743, which are incorporated by reference herein in their entirety.

In an embodiment of the invention, the WEE1 inhibitor for use in the instant invention is WEE1-2, the structure of which is as shown below.

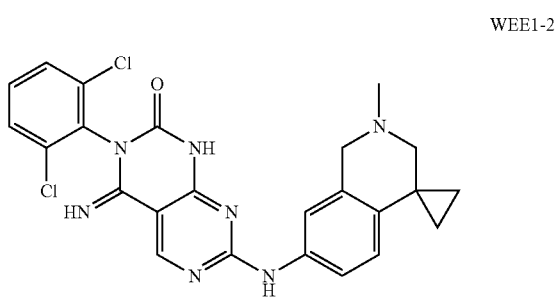 [SMILES: CN1Cc2cc(Nc3ncc4c(=N)n(-c5c(Cl)cccc5Cl)c(=O)[nH]c4n3)ccc2C2(CC2)C1]

WEE1-2

WEE1-2 is a WEE1 inhibitor which is useful for the treatment of cancer. WEE1-2 is also known as 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. WEE1-2 has been described in PCT International Publication WO2008/153207 and US Publication US2011-0135601, which are incorporated by reference herein in their entirety. Crystalline forms of WEE1-2 are described in International Publication WO2009/151997 and US Publication US2011-0092520.

In one embodiment, the WEE1 inhibitor is

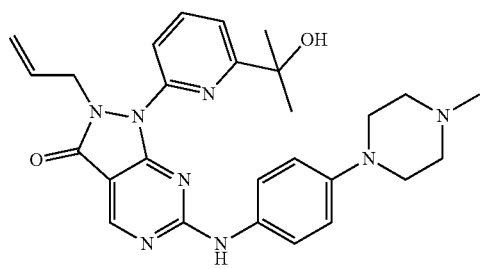 [SMILES: C=CCn1c(=O)c2cnc(Nc3ccc(N4CCN(C)CC4)cc3)nc2n1-c1cccc(C(C)(C)O)n1]

or a pharmaceutically acceptable salt thereof.

In another embodiment, the WEE1 inhibitor is

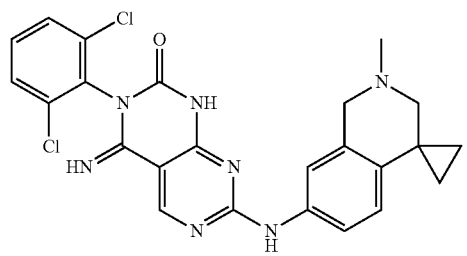

or a pharmaceutically acceptable salt thereof.

The compounds used in the methods of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

In the compounds used in the methods of the present invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds disclosed herein. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds disclosed herein can be prepared without undue experimentation by conventional techniques well known to those skilled in the art.

The WEE1 inhibitors used in the methods of the instant invention may also exist as various crystals, amorphous substances, pharmaceutically acceptable salts, hydrates and solvates. Further, the WEE1 inhibitors of the instant invention may be provided as prodrugs. In general, such prodrugs are functional derivatives of the WEE1 inhibitors of the instant invention that can be readily converted into compounds that are needed by living bodies. Accordingly, in the method of treatment of various cancers in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of the compound may include active compounds that are produced by putting the compound in a biological environment, and are within the scope of the compound in the invention.

In one embodiment of the invention, the WEE1 inhibitor is administered in a dose between 100 mg per day and 250 mg per day. In another embodiment of the invention, the WEE1 inhibitors may be dosed twice a day (BID) over the course of two and a half days (for a total of 5 doses) or once a day (QD) over the course of two days (for a total of 2 doses).

In another embodiment of the invention, the WEE1 inhibitor is administered in a dose between 200 mg per day and 400 mg per day, and preferably 250-350 mg per day. In an embodiment of the invention, the WEE1 inhibitors may be dosed once a day (QD) over the course of five days.

Method of Treating Cancer

Cancers that may be treated by the WEE1 inhibitors include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

The term "WEE1 kinase associated cancer" as referred to in this description means a cancer associated with the activity or inhibition of WEE1 kinases including, but not limited to, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma, or as sensitizers for chemo therapy or radiation therapy of those cancers. In particular, the WEE1 inhibitor of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma, or as sensitizers for chemotherapy or radiation therapy of those cancers.

In another embodiment, the cancer is selected from the group consisting of ovarian cancer, melanoma, lung cancer, colorectal cancer, colon cancer, rectum cancer, prostate cancer, and breast cancer.

In a further embodiment, the cancer is selected from the group consisting of ovarian carcinoma, ovary clear cell carcinoma, ovary adenocarcinoma, ovary teratocarcinoma, skin malignant melanoma, malignant melanoma, lung carcinoma, large cell lung cancer, lung adenocarcinoma, non-small cell lung cancer, lung squamous cell carcinoma, colorectal carcinoma, colorectal adenocarcinoma, colon carcinoma, rectum adenocarcinoma, prostate carcinoma, breast ductal carcinoma and breast cancer.

In yet another embodiment, the cancer is ovarian cancer. In a further embodiment, the cancer is lung cancer.

In another embodiment of the invention, a method of inhibiting or modulating WEE1 activity in a patient is provided.

The term "treatment of cancer" as referred to in this description means that an anti-cancer agent is administered to a cancer patient so as to inhibit the growth of the cancer cells in the patient.

The term "patient" or "subject" as referred to in this description means the recipient in need of medical intervention or treatment. Mammalian and non-mammalian patients or subjects are included.

Combination Therapy

Combinations of the WEE1 inhibitors with therapeutic, chemotherapeutic and anti-cancer agents in the methods of the invention are within the scope of the invention. The WEE1 inhibitors may also be administered in combination with one or more additional anti-cancer agents, wherein the amounts of the WEE1 inhibitor and the anti-cancer agent result in a therapeutic effect. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The WEE1 inhibitors may also be useful when co-administered with radiation therapy. The WEE1 inhibitors can be present in the same dosage unit as the anticancer agent or in separate dosage units.

Non-limiting examples of suitable anti-cancer agents include cytostatic agents, cytotoxic agents, targeted therapeutic agents (small molecules, biologics, siRNA and microRNA) against cancer and neoplastic diseases as follows:

1) anti-metabolites (such as methoxtrexate, 5-fluorouracil, gemcitabine, fludarabine, capecitabine);
2) alkylating agents, such as temozolomide and cyclophosphamide,
3) DNA interactive and DNA damaging agents, such as cisplatin, oxaliplatin and doxorubicin,
4) Ionizing irradiation, such as radiation therapy,
5) topoisomerase II inhibitors, such as etoposide and doxorubicin,
6) topoisomerase I inhibitors, such as irinotecan and topotecan,
7) tubulin interacting agents, such as paclitaxel, docetaxel, abraxane and epothilones,
8) kinesin spindle protein inhibitors,
9) spindle checkpoint inhibitors,
10) poly(ADP-ribose) polymerase (PARP) inhibitors, such as olaparib, MK-4827 and veliparib,
11) matrix metalloprotease (MMP) inhibitors,
12) protease inhibitors, such as cathepsin D and cathepsin K inhibitors,
13) proteosome or ubiquitination inhibitors, such as bortezomib,
14) activators of mutant p53 to restore its wild-type p53 activity,
15) adenoviral-p53,
16) Bcl-2 inhibitors, such as ABT-263,
17) heat shock protein (HSP) modulators, such as geldanamycin and 17-AAG,
18) histone deacetylase (HDAC) inhibitors, such as vorinostat (SAHA),
19) sex hormone modulating agents,
   a. anti-estrogens, such as tamoxifen and fulvestrant,
   b. selective estrogen receptor modulators (SERM), such as raloxifene,
   c. anti-androgens, such as bicalutamide and flutamide,
   d. LHRH agonists, such as leuprolide,
   e. 5α-reductase inhibitors, such as finasteride,
   f. cytochrome P450 C17 lyase (CYP450c17, also called 17α-hydroxylase/17,20 lysase) inhibitors, such as abiraterone acetate, VN/124-1 and TAK-700,
   g. aromatase inhibitors, such as letrozole, anastrozole and exemestane,
20) EGFR kinase inhibitors, such as geftinib, erlotinib and laptinib,
21) dual erbB1 and erbB2 inhibitors, such as lapatinib,
22) multi-targeted kinases (serine/threonine and/or tyrosine kinase) inhibitors,
   a. ABL kinase inhibitors, imatinib, nilotinib and dasatinib,
   b. VEGFR-1, VEGFR-2, PDGFR, KDR, FLT, c-Kit, Tie2, Raf, MEK and ERK inhibitors, such as sunitinib, sorafenib, vandetanib, pazopanib, PLX-4032, axitinib, PTK787 and GSK-1120212,
   c. polo-like kinase inhibitors,
   d. aurora kinase inhibitors,
   e. JAK inhibitors,
   f. c-MET kinase inhibitors,
   g. cyclin-dependent kinase inhibitors, such as CDK1 and CDK2 inhibitor SCH 727965,
   h. PI3K and mTOR inhibitors, such as GDC-0941, BEZ-235, BKM-120 and AZD-8055, i. rapamycin and its analogs, such as temsirolimus, everolimus, and deforolimus 23) and other anti-cancer (also know as anti-neoplastic) agents include but are not limited to ara-C, adriamycin, cytoxan, carboplatin, uracil mustard, clormethine, ifosfsmide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, vinorelbine, navelbine, bleomycin, dactinomycin, daunorubicin, doxorubicin, epirubicin, teniposide, cytarabine, pemetrexed, idarubicin, mithramycin, deoxycoformycin, mitomycin-C, l-asparaginase, teniposide, ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, flutamide medroxyprogesteroneacetate, toremifene, goserelin, carboplatin, hydroxyurea, amsacrine, procarbazine, mitotane, mitoxantrone, levamisole, drolloxafine, hexamethylmelamine, bexxar, zevalin, trisenox, profimer, thiotepa, altretamine, doxil, ontak, depocyt, aranesp, neupogen, neulasta and kepivance, 24) farnesyl protein transferase inhibitors, such as, SARASAR™(4-[2-[4-[(11R)-3,10-dibromo-8-chloro-6, 11-dihydro-5H-benzo[5,6]cyclohepta[1,2-b]pyridin-11-yl-]-1-piperidinyl]-2-oxoethyl]-piperidinecarboxamide and tipifarnib, 25) interferons, such as Intron A and Peg-Intron, 26) anti-erbB1 antibodies, such as cetuximab and panitumumab, 27) anti-erbB2 antibodies, such as trastuzumab, 28) anti-CD52 antibodies, such as alemtuzumab, 29) anti-CD20 antibodies, such as rituximab, 30) anti-CD33 antibodies, such as gemtuzumab ozogamicin, 31) anti-VEGF antibodies, such as avastin, 32) TRIAL ligands, such as lexatumumab, mapatumumab, and AMG-655, 33) anti-CTLA-4 antibodies, such as ipilimumab, 34) antibodies against CTA1, CEA, CD5, CD19, CD22, CD30, CD44, CD44V6, CD55, CD56, EpCAM, FAP, MHCII, HGF, IL-6, MUC1, PSMA, TAL6, TAG-72, TRAILR, VEGFR, IGF-2 and FGF, and 35) anti-IGF-1R antibodies, such as dalotuzumab (MK-0646) and robatumumab (SCH 717454).

If formulated as a fixed dose such combination products employ the WEE1 inhibitor administered in the invention within the dosage range described herein and the other pharmaceutically active agent or treatment within its dosage range. The WEE1 inhibitor may also be administered sequentially with known anticancer or cytotoxic agents when a combination formulation is inappropriate. The invention is not limited in the sequence of administration; the WEE1 inhibitor may be administered either concurrent with, prior to or after administration of the known anticancer or cytotoxic agent. Such techniques are within the skills of the persons skilled in the art as well as attending physicians.

Accordingly, in an aspect, this invention includes combinations for use in the invention comprising an amount of a WEE1 inhibitor, or a pharmaceutically acceptable salt thereof, and an amount of one or more anti-cancer treatments and anti-cancer agents listed above or below wherein the amounts of the compounds/treatments result in potential therapeutic effect. In one embodiment, the anti-cancer agent is selected from the group consisting of: 5-FU, carboplatin, doxorubicin, etoposide, gemcitabine, irinotecan, mitomycin, temozolmide and topotecan. In another embodiment, the anti-cancer agent is carboplatin. In another embodiment, the anti-cancer agents are carboplatin and paclitaxel.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mitosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032).

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24): 5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabin furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer, Vol.* 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105: 141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with WEE1 inhibitors include agents that modulate or inhibit the coagulation and fibrinolysis systems (see review in *Clin. Chem. La. Med.* 38: 679-692 (2000)). Examples of such agents that modulate or inhibit the coagulation and fibrinolysis pathways include, but are not limited to, heparin (see *Thromb. Haemost.* 80: 10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411: 355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the WEE1 inhibitor with PPAR-γ (i.e., PPAR-gamma) agonists and PPAR-δ (i.e., PPAR-delta) agonists may be useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31: 909-913; *J. Biol. Chem.* 1999; 274: 9116-9121; *Invest. Ophthalmol Vis. Sci.* 2000; 41: 2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119: 709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy)propoxy)-2-ethylchromane-2-carboxylic acid.

Another embodiment of the instant invention is the use of WEE1 inhibitors in combination with gene therapy for the potential treatment of cancer. For an overview of genetic strategies to treating cancer see Hall et al (*Am. J. Hum. Genet.* 61: 785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8): 1105-13), and interferon gamma (*J. Immunol.* 2000; 164: 217-222).

The invention disclosed herein is exemplified by the following examples which should not be construed to limit the scope of the disclosure.

EXAMPLES

Example 1

Thirty-one cell lines were treated with various DNA-damaging agents with or without WEE1-1 in a cell growth assay. Immediately after cells were plated, each drug was added at four concentrations for a total of 16 treatment conditions per combination (4×4 dose grid). Ninety-six hours following treatment, cell growth was evaluated with CellTiter-Glo (Promega) in treated samples relative to vehicle (DMSO) treated samples. Synergy was quantitated as the predicted additive growth inhibition of the two drugs (using the Bliss additivity model) subtracted from the observed growth inhibition of the two drugs. Therefore, a larger positive net difference indicates greater synergy, a negative difference indicates antagonism, and values at or close to 0 indicate additivity predicted by the Bliss model. The scale is displayed in the upper left corner of FIG. 1; darkest grey denotes strong synergy, light grey denotes moderate synergy, and darker grey denotes values that are considered additive, not synergistic. Each column represents a different cell line; each row represents a pairing between WEE1-1 and different DNA-damaging agents. The cell line name is shown above the column and the tissue type from which the cell line was derived is at the bottom of the column. The 12 leftmost columns represent cell lines that are reported to be TP53 wildtype; the 19 rightmost columns represent cell lines that are reported to have mutations in TP53. Data are summarized in the table to the right. The p53+/+ column summarizes the percentage of p53+/+ cell lines that exhibited synergy in the assay (i.e., the number of darkest grey and light grey squares in a row divided by 12).

The p53−/− column summarizes the percentage of p53−/− cell lines that exhibited synergy in the assay (i.e., the number of darkest grey and light grey squares in a row divided by 19). Overall, the percentage of p53 wildtype cell lines that exhibited synergy was 15/(12×9)=14%; the percentage of P53 mutant cell lines that exhibited synergy was 50/(19×9) =29%. Thus, in combination with DNA-damaging agents, WEE1-1 is more likely to lead to synergistic growth inhibition in cell lines defective in TP53.

Example 2

Identification of Loss of Function Mutations

A multiple-step approach to develop a list of mutations which would be most likely to result in a non-functional p53 protein was implemented. First, different types of mutations predicted to result in p53 loss-of-function were assigned a relative point value, as shown in the Table 1 below. For example, three points were assigned for any mutation that results in a truncation, frameshift or a splice site defect that would completely eliminate the DNA binding domain of p53, i.e., before amino acid 306. (A frameshift mutation is one that causes the ribosome to use a different reading frame on the mRNA. For example, frameshifts can occur from one or two basepair insertions or deletions). Second, published data in the International Agency for Research on Cancer (IARC) database (A. Petijean et al. *Hum Mutat.* 2007, 28(6): 622-9) was used to assess the impact of each possible mutation on p53 function (dominant negative protein or transactivation function). Mutations shown to display dominant negative activity in a model system were assigned a point value of 2.0 points, while mutations reducing or eliminating the protein's transactivation function were assigned a value of 1 point. Third, data from an internal gene expression database and the Cell line Biomarker Discovery (CBD) expression database of 650 cancer cell lines was used to identify mutations in TP53 that resulted in gene expression patterns indicative of p53 loss-of-function. These mutations were assigned 1 point. Finally, mutational analysis of tumor samples reported to the IARC database was used to identify mutations that were observed in more than 10 somatic (i.e., tumor) samples, which were assigned a point value of 0.5 points.

TABLE 1

| Type of Mutation | Point Value |
|---|---|
| Stop codon mutation (truncated protein) prior to codon 306 | 3 |
| Splice site mutation between codons 97 and 375 | 3 |
| Frameshift mutation | 3 |
| Dominant negative mutation | 2 |
| P53 signature score p-value < 0.05 vs WT | 1 |
| Transactivation loss-of-function mutation | 1 |
| Mutation reported > 10 times in somatic tissue at nucleotide level | 0.5 |
| Mutation reported > 10 times in somatic tissue at amino acid level | 0.5 |

TABLE 2

| Mutation Lookup Table | | | | | | | | | | |
|---|---|---|---|---|---|---|---|---|---|---|
| E2* | K120* | V143M | A159D | C176F | R196P | C229* | C242S | R249S | C275G | R282G |
| E3* | C124* | V143A | A161D | C176Y | V197G | Y234H | C242* | P250L | C275Y | R282W |
| Q5* | Y126* | Q144* | Y163N | C176S | E198* | Y234C | C242W | I255F | C275F | R282P |

TABLE 2-continued

Mutation Lookup Table

| | | | | | | | | | |
|---|---|---|---|---|---|---|---|---|---|
| S6* | S127P | L145Q | Y163H | C176* | G199* | Y234* | G244S | L257Q | C275S | R282Q |
| E11* | S127T | L145P | Y163D | C176W | G199E | Y236D | G244C | L257P | C275* | R283H |
| Q16* | S127F | W146* | Y163C | P177S | L201* | Y236H | G244R | E258* | C275W | R283P |
| E17* | S127Y | D148* | Y163S | P177H | E204* | Y236N | G244D | E258K | A276P | E285* |
| S20* | S127C | P151T | Y163* | P177R | Y205D | Y236C | G244V | D259Y | C277Y | E285K |
| W23* | K132* | P151S | K164* | H179N | Y205S | Y236S | G244A | D259V | C277F | E285V |
| I(24* | K132Q | P151A | K164E | H179Y | Y205C | Y236* | G245S | N263* | C277* | E286* |
| E28* | K132E | P151R | Q165* | H179R | Y205* | M2371 | G245R | L265P | P278T | E286K |
| L35* | K132R | P151H | S166* | H179L | L206* | C238R | G245C | G266* | P278S | E286Q |
| Q38* | K132M | P152S | Q167* | H179Q | R209* | C238Y | G245D | G266R | P278A | E286G |
| L43* | K132T | P152L | H168Y | H179* | R213* | C238F | G245V | G266E | P278H | E286V |
| E51* | K132N | G154V | H168R | E180* | R213Q | C238* | G245A | G266V | P278L | E286A |
| Q52* | M133P | T155P | H168P | C182* | R213L | N239D | M246V | R267W | P278R | E286D |
| W53* | C135R | T155N | H168L | S183* | H214R | N239S | M246L | R267P | G279E | E287* |
| E56* | C135S | R156P | E171* | S183* | S2151 | N239* | M246R | F270C | R280* | N288D |
| E62* | C135G | V157F | V173M | Q192* | V216M | S240G | N2471 | E271* | R280G | K291* |
| R65* | C135Y | V157L | V173L | H193Y | V216L | S241T | N247T | V272M | R280T | K292* |
| E68* | C135F | V157D | V173G | H193D | V216E | S241A | R248W | R273C | R280K | E294* |
| W91* | C135S | V157G | V173E | H193N | V216G | S241P | R248G | R273S | R2801 | E298* |
| S94* | C135* | V157A | R175G | H193L | Y220N | S241F | R248Q | R273G | R280S | K305* |
| Q100* | C135W | R158G | R175C | H193P | Y220H | S241C | R248L | R273H | D281N | R306* |
| K101* | Q136* | R158S | R175H | H193R | Y220D | S241Y | R248P | R273L | D281Y | R337C |
| Y103* | A138P | R158P | R175L | L194F | Y220C | C242S | R249W | R273P | D281H | |
| Q104* | A138G | R158H | R175P | L194R | Y220S | C242R | R249G | V274F | D281G | |
| Y107* | K139* | R158L | C176R | I195F | Y220* | C242G | R249M | V274A | D281V | |
| R110L | C141Y | A159P | C176S | I195T | E221* | C242Y | R249K | C275R | D281A | |
| L114* | C141* | A159V | C176G | R196* | E224* | C242F | R249T | C275S | D281E | |

PLUS ANY MUTATIONS LABELED "FRAMESHIFT" OR "SPLICE DEFECT"

*Denotes stop codon; The GENBANK accession number of the p53 protein is NM000546. The GENBANK accession number of the TP53 gene is X54156.1

The TP53 mutations in the look-up table (Table 2) include those whose evidence score is 2.0 or greater. The expanded table of TP53 mutations (Table 3) shows the location and type of mutation, as well as the point value assigned to the mutation.

TABLE 3

Supporting evidence for mutations in the Mutation Lookup Table

| NtNum | Codon | WT Codon | Mutant Codon | Protein Change | Stop Codon (3 pts) | Splice Defect (3 pts) | Dominant Negative (2 pts) | Trans-activation (1 pt) | P53 Signature P-Value | P53 signature p value <0.05 (1 pt) | Reported >10x in somatic @ AA level (0.5 pt) | Reported >10x in somatic @ Base level (0.5 pt) | Evidence Score |
|---|---|---|---|---|---|---|---|---|---|---|---|---|---|
| 11009 | 2 | GAG | TAG | E2* | Yes | | | | | | | 0 | 3 |
| 11012 | 3 | GAG | TAG | E3* | Yes | | | | | | | 0 | 3 |
| 11018 | 5 | CAG | TAG | Q5* | Yes | | | | | | | 1 | 3 |
| 11022 | 6 | TCA | TAA | S6* | Yes | | | | | | | 0 | 3 |
| 11022 | 6 | TCA | TGA | S6* | Yes | | | | | | | 0 | 3 |
| 11036 | 11 | GAG | TAG | E11* | Yes | | | | | | | 0 | 3 |
| 11051 | 16 | CAG | TAG | Q16* | Yes | | | | | | | 0 | 3 |
| 11054 | 17 | GAA | TAA | E17* | Yes | | | | | | | 0 | 3 |
| 11064 | 20 | TCA | TAA | S20* | Yes | | | | | | | 0 | 3 |
| 11064 | 20 | TCA | TGA | S20* | Yes | | | | | | | 0 | 3 |
| 11073 | 23 | TGG | TAG | W23* | Yes | | | | | | | 0 | 3 |
| 11074 | 23 | TGG | TGA | W23* | Yes | | | | | | | 0 | 3 |
| 11075 | 24 | AAA | TAA | K24* | Yes | | | | | | | 0 | 3 |
| 11204 | 28 | GAA | TAA | E28* | Yes | | | | | | | 0 | 3 |
| 11335 | 35 | TTG | TAG | L35* | Yes | | | | | | | 0 | 3 |
| 11343 | 38 | CAA | TAA | Q38* | Yes | | | | | | | 3 | 3 |
| 11359 | 43 | TTG | TAG | L43* | Yes | | | | | | | 3 | 3 |
| 11382 | 51 | GAA | TAA | E51* | Yes | | | | | | | 6 | 3 |
| 11385 | 52 | CAA | TAA | Q52* | Yes | | | | | | | 8 | 3 |
| 11389 | 53 | TGG | TAG | W53* | Yes | | | | | | | 7 | 3 |
| 11390 | 53 | TGG | TGA | W53* | Yes | | | | | | | 10 | 3 |
| 11397 | 56 | GAA | TAA | E56* | Yes | | | | | | | 6 | 3 |
| 11415 | 62 | GAA | TAA | E62* | Yes | | | | | | | 9 | 3 |
| 11424 | 65 | AGA | TGA | R65* | Yes | | | | | | | 3 | 3 |
| 11433 | 68 | GAG | TAG | E68* | Yes | | | | | | | 6 | 3 |
| 11503 | 91 | TGG | TAG | W91* | Yes | | | | | | | 13 | 3.5 |

TABLE 3-continued

Supporting evidence for mutations in the Mutation Lookup Table

| | | | | | | | | | | | | |
|---|---|---|---|---|---|---|---|---|---|---|---|---|
| 11504 | 91 | TGG | TGA | W91* | Yes | | | | | | 12 | 3.5 |
| 11512 | 94 | TCA | TAA | S94* | Yes | | | | | | 2 | 3 |
| 11512 | 94 | TCA | TGA | S94* | Yes | | | | | | 2 | 3 |
| 11529 | 100 | CAG | TAG | Q100* | Yes | | | | | | 16 | 3.5 |
| 11532 | 101 | AAA | TAA | K101* | Yes | | | | | | 1 | 3 |
| 11540 | 103 | TAC | TAA | Y103* | Yes | | | | | | 3 | 3 |
| 11540 | 103 | TAC | TAG | Y103* | Yes | | | | | | 1 | 3 |
| 11541 | 104 | CAG | TAG | Q104* | Yes | | | | | | 16 | 3.5 |
| 11552 | 107 | TAC | TAA | Y107* | Yes | | | | | | 4 | 3 |
| 11552 | 107 | TAC | TAG | Y107* | Yes | | | | | | 5 | 3 |
| 11560 | 110 | CGT | CTT | R110L | | | Non functional | 1.00E−01 | | 18 | 30 | 2 |
| 11572 | 114 | TTG | TAG | L114* | Yes | | | | | | 3 | 3 |
| 11589 | 120 | AAG | TAG | K120* | Yes | | | | | | 2 | 3 |
| 11603 | 124 | TGC | TGA | C124* | Yes | | | | | | 1 | 3 |
| 12366 | 126 | TAC | TAA | Y126* | Yes | | | | | | 12 | 3.5 |
| 12366 | 126 | TAC | TAG | Y126* | Yes | | | | | | 13 | 3.5 |
| 12367 | 127 | TCC | CCC | S127P | | Yes | Non functional | 1.00E−02 | Yes | 3 | 6 | 4 |
| 12367 | 127 | TCC | ACC | S127T | | | Non functional | 1.00E−02 | Yes | | 3 | 2 |
| 12368 | 127 | TCC | TTC | S127F | | | Non functional | 1.00E−02 | Yes | 2 | 23 | 2.5 |
| 12368 | 127 | TCC | TAC | S127Y | | | Non functional | 1.00E−02 | Yes | 5 | 9 | 2 |
| 12368 | 127 | TCC | TGC | S127C | | | Non functional | 1.00E−02 | Yes | 1 | 2 | 2 |
| 12382 | 132 | AAG | TAG | K132* | Yes | | | 7.00E−04 | Yes | | 2 | 4 |
| 12382 | 132 | AAG | CAG | K132Q | | | Non functional | 7.00E−04 | Yes | 12 | 17 | 3 |
| 12382 | 132 | AAG | GAG | K132E | | | Non functional | 7.00E−04 | Yes | 16 | 24 | 3 |
| 12383 | 132 | AAG | AGG | K132R | | Yes | Non functional | 7.00E−04 | Yes | 30 | 57 | 5 |
| 12383 | 132 | AAG | ATG | K132M | | | Non functional | 7.00E−04 | Yes | 7 | 12 | 2.5 |
| 12383 | 132 | AAG | ACG | K132T | | | Non functional | 7.00E−04 | Yes | 3 | 4 | 2 |
| 12384 | 132 | AAG | AAT | K132N | | Yes | Non functional | 7.00E−04 | Yes | 22 | 26 | 5 |
| 12384 | 132 | AAG | AAC | K132N | | Yes | Non functional | 7.00E−04 | Yes | 22 | 34 | 5 |
| 12386 | 133 | ATG | AAG | M133K | | | Non functional | 2.00E−01 | | 11 | 20 | 2 |
| 12391 | 135 | TGC | CGC | C135R | | | Non functional | 2.00E−02 | Yes | 5 | 16 | 2.5 |
| 12391 | 135 | TGC | AGC | C135S | | | Non functional | 2.00E−02 | Yes | 4 | 8 | 2 |
| 12391 | 135 | TGC | GGC | C135G | | | Non functional | 2.00E−02 | Yes | 6 | 9 | 2 |
| 12392 | 135 | TGC | TAC | C135Y | | Yes | Non functional | 2.00E−02 | Yes | 46 | 80 | 5 |
| 12392 | 135 | TGC | TTC | C135F | | | Non functional | 2.00E−02 | Yes | 34 | 56 | 3 |
| 12392 | 135 | TGC | TCC | C135S | | | Non functional | 2.00E−02 | Yes | 4 | 8 | 2 |
| 12393 | 135 | TGC | TGA | C135* | Yes | | | 2.00E−02 | Yes | | 8 | 4 |
| 12393 | 135 | TGC | TGG | C135W | | | | 2.00E−02 | Yes | 17 | 26 | 2 |
| 12394 | 136 | CAA | TAA | Q136* | Yes | | | | | | 39 | 3.5 |
| 12400 | 138 | GCC | CCC | A138P | | | Non functional | 4.00E−02 | Yes | 12 | 30 | 3 |
| 12401 | 138 | GCC | GGC | A138G | | | Non functional | 4.00E−02 | Yes | | 0 | 2 |
| 12403 | 139 | AAG | TAG | K139* | Yes | | | | | | 5 | 3 |
| 12410 | 141 | TGC | TAC | C141Y | | | Non functional | 5.00E−01 | | 61 | 97 | 2 |
| 12411 | 141 | TGC | TGA | C141* | Yes | | | 5.00E−01 | | 19 | 3.5 | |
| 12415 | 143 | GTG | ATG | V143M | | | Non functional | 1.00E−01 | | 15 | 30 | 2 |
| 12416 | 143 | GTG | GCG | V143A | | | Non functional | 1.00E−01 | | 13 | 20 | 2 |
| 12418 | 144 | CAG | TAG | Q144* | Yes | | | | | | 44 | 3.5 |
| 12422 | 145 | CTG | CAG | L145Q | | | Non functional | | | 14 | 19 | 2 |
| 12422 | 145 | CTG | CCG | L145P | | | Non functional | | | 15 | 21 | 2 |
| 12425 | 146 | TGG | TAG | W146* | Yes | | | | | | 50 | 3.5 |
| 12426 | 146 | TGG | TGA | W146* | Yes | | | | | | 51 | 3.5 |

TABLE 3-continued

Supporting evidence for mutations in the Mutation Lookup Table

| | | | | | | | | | | | | |
|---|---|---|---|---|---|---|---|---|---|---|---|---|
| 12432 | 148 | GAT | TGA | D148* | Yes | | Non functional | 6.00E-03 | Yes | | | 4 |
| 12439 | 151 | CCC | ACC | P151T | | | Non functional | 6.00E-03 | Yes | 13 | 21 | 3 |
| 12439 | 151 | CCC | TCC | P151S | | | Non functional | 6.00E-03 | Yes | 58 | 95 | 3 |
| 12439 | 151 | CCC | GCC | P151A | | | Non functional | 6.00E-03 | Yes | 7 | 18 | 2.5 |
| 12440 | 151 | CCC | CGC | P151R | | Yes | Non functional | 6.00E-03 | Yes | 6 | 20 | 4.5 |
| 12440 | 151 | CCC | CAC | P151H | | | Non functional | 6.00E-03 | Yes | 1 | 36 | 2.5 |
| 12442 | 152 | CCG | TCG | P152S | | | Non functional | 6.00E-01 | | 21 | 30 | 2 |
| 12442 | 152 | CCG | CTG | P152L | | | Non functional | 6.00E-03 | Yes | 84 | 10 | 3 |
| 12449 | 154 | GGC | GTC | G154V | | | Non functional | 4.00E-01 | | 34 | 64 | 2 |
| 12451 | 155 | ACC | CCC | T155P | | | Non functional | 1.00E-01 | | 13 | 21 | 2 |
| 12452 | 155 | ACC | AAC | T155N | | | Non functional | 1.00E-01 | | 19 | 32 | 2 |
| 12455 | 156 | CGC | CCC | R156P | | | Non functional | 8.00E-01 | | 23 | 44 | 2 |
| 12457 | 157 | GTC | TTC | V157F | | | Non functional | 1.00E-02 | Yes | 133 | 186 | 3 |
| 12457 | 157 | GTC | CTC | V157L | | | Non functional | 1.00E-02 | Yes | 6 | 9 | 2 |
| 12458 | 157 | GTC | GAC | V157D | | | Non functional | 1.00E-02 | Yes | 8 | 14 | 2.5 |
| 12458 | 157 | GTC | GGC | V157G | | | Non functional | 1.00E-02 | Yes | 7 | 12 | 2.5 |
| 12458 | 157 | GTC | GCC | V157A | | | Non functional | 1.00E-02 | Yes | 1 | 2 | 2 |
| 12460 | 158 | CGC | GGC | R158G | | | Non functional | 4.00E-03 | Yes | 10 | 22 | 2.5 |
| 12460 | 158 | CGC | AGC | R158S | | | Non functional | 4.00E-03 | Yes | | 4 | 2 |
| 12461 | 158 | CGC | CCC | R158P | | Yes | Non functional | 4.00E-03 | Yes | 9 | 19 | 4.5 |
| 12461 | 158 | CGC | CAC | R158H | | | Non functional | 4.00E-03 | Yes | 55 | 106 | 3 |
| 12461 | 158 | CGC | CTC | R158L | | | Non functional | 4.00E-03 | Yes | 1 | 96 | 2.5 |
| 12463 | 159 | GCC | CCC | A159P | | | Non functional | 3.00E-03 | Yes | 13 | 30 | 3 |
| 12464 | 159 | GCC | GTC | A159V | | | Non functional | 3.00E-03 | Yes | 28 | 46 | 3 |
| 12464 | 159 | GCC | GAC | A159D | | | Non functional | 3.00E-03 | Yes | 6 | 11 | 2.5 |
| 12470 | 161 | GCC | GAC | A161D | | | Non functional | 4.00E-02 | Yes | 7 | 21 | 2.5 |
| 12475 | 163 | TAC | AAC | Y163N | | | Non functional | 2.00E-02 | Yes | 16 | 23 | 3 |
| 12475 | 163 | TAC | CAC | Y163H | | | Non functional | 2.00E-02 | Yes | 16 | 25 | 3 |
| 12475 | 163 | TAC | GAC | Y163D | | | Non functional | 2.00E-02 | Yes | 2 | 4 | 2 |
| 12476 | 163 | TAC | TGC | Y163C | | Yes | Non functional | 2.00E-02 | Yes | 90 | 147 | 5 |
| 12476 | 163 | TAC | TCC | Y163S | | | Non functional | 2.00E-02 | Yes | 4 | 5 | 2 |
| 12477 | 163 | TAC | TAG | Y163* | Yes | | | 2.00E-02 | Yes | | 11 | 4.5 |
| 12477 | 163 | TAC | TAA | Y163* | Yes | | | 2.00E-02 | Yes | | 7 | 4 |
| 12478 | 164 | AAG | TAG | K164* | Yes | | | | | | 17 | 3.5 |
| 12478 | 164 | AAG | GAG | K164E | | | Non functional | | | 11 | 24 | 2 |
| 12481 | 165 | CAG | TAG | Q165* | Yes | | | | | | 45 | 3.5 |
| 12485 | 166 | TCA | TAA | S166* | Yes | | | | | | 15 | 3.5 |
| 12485 | 166 | TCA | TGA | S166* | Yes | | | | | | 15 | 3.5 |
| 12487 | 167 | CAG | TAG | Q167* | Yes | | | | | | 38 | 3.5 |
| 12490 | 168 | CAC | TAC | H168Y | | Yes | | 1.00E-02 | Yes | 9 | 14 | 3.5 |
| 12491 | 168 | CAC | CGC | H168R | | | Non functional | 1.00E-02 | Yes | 12 | 22 | 3 |
| 12491 | 168 | CAC | CCC | H168P | | | Non functional | 1.00E-02 | Yes | 9 | 13 | 2.5 |
| 12491 | 168 | CAC | CTC | H168L | | | Non functional | 1.00E-02 | Yes | 5 | 8 | 2 |

TABLE 3-continued

Supporting evidence for mutations in the Mutation Lookup Table

| | | | | | | | | | | | |
|---|---|---|---|---|---|---|---|---|---|---|---|
| 12499 | 171 | GAG | TAG | E171* | Yes | | | | | 21 | 3.5 |
| 12505 | 173 | GTG | ATG | V173M | | Yes | Non functional | 1.00E-02 | Yes | 35 | 71 | 5 |
| 12505 | 173 | GTG | TTG | V173L | | Yes | Non functional | 1.00E-02 | Yes | 9 | 65 | 4.5 |
| 12505 | 173 | GTG | CTG | V173L | | Yes | Non functional | 1.00E-02 | Yes | 9 | 21 | 4.5 |
| 12506 | 173 | GTG | GGG | V173G | | | Non functional | 1.00E-02 | Yes | 4 | 16 | 2.5 |
| 12506 | 173 | GTG | GAG | V173E | | | Non functional | 1.00E-02 | Yes | 1 | 3 | 2 |
| 12511 | 175 | CGC | GGC | R175G | | | Non functional | 9.00E-13 | Yes | 11 | 24 | 3 |
| 12511 | 175 | CGC | TGC | R175C | | | | 9.00E-13 | Yes | 12 | 27 | 2 |
| 12512 | 175 | CGC | CAC | R175H | | Yes | Non functional | 9.00E-13 | Yes | 691 | 1158 | 5 |
| 12512 | 175 | CGC | CTC | R175L | | | | 9.00E-13 | Yes | 18 | 27 | 2 |
| 12512 | 175 | CGC | CCC | R175P | | | Non functional | 9.00E-13 | Yes | 5 | 8 | 2 |
| 12514 | 176 | TGC | CGC | C176R | | Yes | Non functional | 2.00E-03 | Yes | 8 | 14 | 4.5 |
| 12514 | 176 | TGC | AGC | C176S | | | Non functional | 2.00E-03 | Yes | 1 | 20 | 2.5 |
| 12514 | 176 | TGC | GGC | C176G | | | Non functional | 2.00E-03 | Yes | 3 | 7 | 2 |
| 12515 | 176 | TGC | TTC | C176F | | Yes | | 2.00E-03 | Yes | 1 | 156 | 3.5 |
| 12515 | 176 | TGC | TAC | C176Y | | | Non functional | 2.00E-03 | Yes | 44 | 89 | 3 |
| 12515 | 176 | TGC | TCC | C176S | | | Non functional | 2.00E-03 | Yes | 1 | 11 | 2.5 |
| 12516 | 176 | TGC | TGA | C176* | Yes | | | 2.00E-03 | Yes | | 9 | 4 |
| 12516 | 176 | TGC | TGG | C176W | | | Non functional | 2.00E-03 | Yes | 11 | 20 | 3 |
| 12517 | 177 | CCC | TCC | P177S | | Yes | | 7.00E-01 | | 8 | 16 | 2.5 |
| 12518 | 177 | CCC | CAC | P177H | | Yes | | 7.00E-01 | | 2 | 5 | 2 |
| 12518 | 177 | CCC | CGC | P177R | | | Non functional | 7.00E-01 | | 13 | 17 | 2 |
| 12523 | 179 | CAT | AAT | H179N | | Yes | | 2.00E-02 | Yes | 13 | 24 | 4 |
| 12523 | 179 | CAT | TAT | H179Y | | Yes | | 2.00E-02 | Yes | 8 | 107 | 3.5 |
| 12524 | 179 | CAT | CGT | H179R | | Yes | Non functional | 2.00E-02 | Yes | 90 | 151 | 5 |
| 12524 | 179 | CAT | CTT | H179L | | Yes | | 2.00E-02 | Yes | 31 | 42 | 4 |
| 12525 | 179 | CAT | CAG | H179Q | | | Non functional | 2.00E-02 | Yes | 7 | 16 | 2.5 |
| 12525 | 179 | CAT | CAA | H179Q | | | Non functional | 2.00E-02 | Yes | 7 | 9 | 2 |
| 12525 | 179 | CAT | TAG | H179* | Yes | | Non functional | 7.00E-01 | | 1 | | 4 |
| 12526 | 180 | GAG | TAG | E180* | Yes | | | 2.00E-01 | | | 19 | 3.5 |
| 12534 | 182 | TGC | TGA | C182* | Yes | | | | | | 7 | 3 |
| 12536 | 183 | TCA | TGA | S183* | Yes | | | | | | 26 | 3.5 |
| 12536 | 183 | TCA | TAA | S183* | Yes | | | | | | 3 | 3 |
| 12643 | 192 | CAG | TAG | Q192* | Yes | | | | | | 96 | 3.5 |
| 12646 | 193 | CAT | TAT | H193Y | | | Non functional | 5.00E-03 | Yes | 25 | 39 | 3 |
| 12646 | 193 | CAT | GAT | H193D | | | Non functional | 5.00E-03 | Yes | 7 | 15 | 2.5 |
| 12646 | 193 | CAT | AAT | H193N | | | Non functional | 5.00E-03 | Yes | 3 | 3 | 2 |
| 12647 | 193 | CAT | CTT | H193L | | | Non functional | 5.00E-03 | Yes | 28 | 60 | 3 |
| 12647 | 193 | CAT | CCT | H193P | | | Non functional | 5.00E-03 | Yes | 12 | 18 | 3 |
| 12647 | 193 | CAT | CGT | H193R | | | Non functional | 5.00E-03 | Yes | 58 | 91 | 3 |
| 12649 | 194 | CTT | TTT | L194F | | | Non functional | 2.00E-01 | | 15 | 27 | 2 |
| 12650 | 194 | CTT | CGT | L194R | | | Non functional | 2.00E-01 | | 26 | 60 | 2 |
| 12652 | 195 | ATC | TTC | I195F | | | Non functional | 3.00E-01 | | 14 | 28 | 2 |
| 12653 | 195 | ATC | ACC | I195T | | | Non functional | 3.00E-01 | | 51 | 89 | 2 |
| 12655 | 196 | CGA | TGA | R196* | Yes | | | 2.00E-01 | | | 223 | 3.5 |
| 12656 | 196 | CGA | CCA | R196P | | | Non functional | 2.00E-01 | | 12 | 19 | 2 |
| 12659 | 197 | GTG | GGG | V197G | | | Non functional | 2.00E-01 | | 14 | 22 | 2 |

TABLE 3-continued

Supporting evidence for mutations in the Mutation Lookup Table

| | | | | | | | | | | |
|---|---|---|---|---|---|---|---|---|---|---|
| 12661 | 198 | GAA | TAA | E198* | Yes | | | | 24 | 3.5 |
| 12664 | 199 | GGA | TGA | G199* | Yes | | 5.00E−01 | | 4 | 3 |
| 12665 | 199 | GGA | GAA | G199E | | Non functional | 5.00E−01 | | 11 15 | 2 |
| 12671 | 201 | TTG | TAG | L201* | Yes | | | | 7 | 3 |
| 12679 | 204 | GAG | TAG | E204* | Yes | | | | 45 | 3.5 |
| 12682 | 205 | TAT | GAT | Y205D | | Non functional | 7.00E−02 | | 13 18 | 2 |
| 12683 | 205 | TAT | TCT | Y205S | | Non functional | 7.00E−02 | | 11 20 | 2 |
| 12683 | 205 | TAT | TGT | Y205C | | Non functional | 7.00E−02 | | 48 110 | 2 |
| 12684 | 205 | TAT | TAA | Y205* | Yes | | 7.00E−02 | | 4 | 3 |
| 12684 | 205 | TAT | TAG | Y205* | Yes | | 7.00E−02 | | 4 | 3 |
| 12686 | 206 | TTG | TAG | L206* | Yes | | | | 11 | 3.5 |
| 12694 | 209 | AGA | TGA | R209* | Yes | | | | 13 | 3.5 |
| 12706 | 213 | CGA | TGA | R213* | Yes | | 6.00E−01 | | 5 | 3 |
| 12707 | 213 | CGA | CAA | R213Q | | Non functional | 6.00E−01 | | 21 36 | 2 |
| 12707 | 213 | CGA | CTA | R213L | | Non functional | 6.00E−01 | | 24 38 | 2 |
| 12710 | 214 | CAT | CGT | H214R | | Non functional | 2.00E−01 | | 41 78 | 2 |
| 12713 | 215 | AGT | ATT | S215I | | Non functional | 9.00E−02 | | 14 25 | 2 |
| 12715 | 216 | GTG | ATG | V216M | | Non functional | 7.00E−04 | Yes | 43 76 | 3 |
| 12715 | 216 | GTG | TTG | V216L | | Non functional | 7.00E−04 | Yes | 7 13 | 2.5 |
| 12715 | 216 | GTG | CTG | V216L | | Non functional | 7.00E−04 | Yes | 7 1 | 2 |
| 12716 | 216 | GTG | GAG | V216E | | Non functional | 7.00E−04 | Yes | 4 7 | 2 |
| 12716 | 216 | GTG | GGG | V216G | | Non functional | 7.00E−04 | Yes | 3 5 | 2 |
| 12727 | 220 | TAT | AAT | Y220N | | Non functional | 4.00E−06 | Yes | 12 17 | 3 |
| 12727 | 220 | TAT | CAT | Y220H | | Non functional | 4.00E−06 | Yes | 7 16 | 2.5 |
| 12727 | 220 | TAT | GAT | Y220D | | Non functional | 4.00E−06 | Yes | 2 3 | 2 |
| 12728 | 220 | TAT | TGT | Y220C | | Non functional | 4.00E−06 | Yes | 186 360 | 3 |
| 12728 | 220 | TAT | TCT | Y220S | | Non functional | 4.00E−06 | Yes | 9 13 | 2.5 |
| 12729 | 220 | TAT | TAA | Y220* | Yes | | 4.00E−06 | Yes | 2 | 4 |
| 12729 | 220 | TAT | TAG | Y220* | Yes | | 4.00E−06 | Yes | 3 | 4 |
| 12730 | 221 | GAG | TAG | E221* | Yes | | | | 11 | 3.5 |
| 12739 | 224 | GAG | TAG | E224* | Yes | | | | 10 | 3 |
| 13324 | 229 | TGT | TGA | C229* | Yes | | | | 7 | 3 |
| 13337 | 234 | TAC | CAC | Y234H | | Non functional | 2.00E−01 | | 12 27 | 2 |
| 13338 | 234 | TAC | TGC | Y234C | | Non functional | 2.00E−01 | | 65 136 | 2 |
| 13339 | 234 | TAC | TAA | Y234* | Yes | | 2.00E−01 | | 11 | 3.5 |
| 13339 | 234 | TAC | TAG | Y234* | Yes | | 2.00E−01 | | 1 | 3 |
| 13343 | 236 | TAC | GAC | Y236D | | Yes Non functional | 1.00E−02 | Yes | 5 8 | 4 |
| 13343 | 236 | TAC | CAC | Y236H | | Non functional | 1.00E−02 | Yes | 7 14 | 2.5 |
| 13343 | 236 | TAC | AAC | Y236N | | | 1.00E−02 | Yes | 11 19 | 2 |
| 13344 | 236 | TAC | TGC | Y236C | | Non functional | 1.00E−02 | Yes | 41 80 | 3 |
| 13344 | 236 | TAC | TCC | Y236S | | Non functional | 1.00E−02 | Yes | 3 3 | 2 |
| 13345 | 236 | TAC | TAA | Y236* | Yes | | 1.00E−02 | Yes | 14 | 4.5 |
| 13345 | 236 | TAC | TAG | Y236* | Yes | | 1.00E−02 | Yes | 8 | 4 |
| 13348 | 237 | ATG | ATA | M237I | | Yes Non functional | 1.00E−01 | | 1 121 | 3.5 |
| 13348 | 237 | ATG | ATT | M237I | | Yes Non functional | 1.00E−01 | | 1 50 | 3.5 |
| 13348 | 237 | ATG | ATC | M237I | | Yes Non functional | 1.00E−01 | | 1 13 | 3.5 |
| 13349 | 238 | TGT | CGT | C238R | | Non functional | 6.00E−01 | | 14 23 | 2 |
| 13350 | 238 | TGT | TAT | C238Y | | Yes Non functional | 6.00E−01 | | 42 85 | 4 |

TABLE 3-continued

Supporting evidence for mutations in the Mutation Lookup Table

| 13350 | 238 | TGT | TTT | C238F |     | Non functional | 6.00E−01 |     | 26  | 40  | 4   |
| --- | --- | --- | --- | --- | --- | --- | --- | --- | --- | --- | --- |
| 13351 | 238 | TGT | TGA | C238* | Yes |                | 6.00E−01 |     | 7   | 3   |     |
| 13352 | 239 | AAC | GAC | N239D |     | Non functional |          |     | 25  | 48  | 2   |
| 13353 | 239 | AAC | AGC | N239S | Yes | Non functional |          |     | 1   | 31  | 3.5 |
| 13355 | 240 | AGT | GGT | S240G |     | Non functional |          |     | 13  | 18  | 2   |
| 13358 | 241 | TCC | ACC | S241T | Yes | Non functional | 3.00E−06 | Yes | 5   | 9   | 4   |
| 13358 | 241 | TCC | GCC | S241A |     | Non functional | 3.00E−06 | Yes | 6   | 12  | 2.5 |
| 13358 | 241 | TCC | CCC | S241P |     | Non functional | 3.00E−06 | Yes | 3   | 10  | 2   |
| 13359 | 241 | TCC | TTC | S241F | Yes | Non functional | 3.00E−06 | Yes | 5   | 100 | 4.5 |
| 13359 | 241 | TCC | TGC | S241C |     | Non functional | 3.00E−06 | Yes | 23  | 35  | 3   |
| 13359 | 241 | TCC | TAC | S241Y |     | Non functional | 3.00E−06 | Yes | 6   | 19  | 2.5 |
| 13361 | 242 | TGC | AGC | C242S |     | Non functional | 6.00E−03 | Yes | 10  | 14  | 2.5 |
| 13361 | 242 | TGC | CGC | C242R |     | Non functional | 6.00E−03 | Yes | 10  | 13  | 2.5 |
| 13361 | 242 | TGC | GGC | C242G |     | Non functional | 6.00E−03 | Yes | 2   | 7   | 2   |
| 13362 | 242 | TGC | TAC | C242Y | Yes | Non functional | 6.00E−03 | Yes | 35  | 54  | 5   |
| 13362 | 242 | TGC | TTC | C242F | Yes | Non functional | 6.00E−03 | Yes | 1   | 88  | 4.5 |
| 13362 | 242 | TGC | TCC | C242S |     | Non functional | 6.00E−03 | Yes | 10  | 19  | 2.5 |
| 13363 | 242 | TGC | TGA | C242* | Yes |                | 6.00E−03 | Yes |     | 4   | 4   |
| 13363 | 242 | TGC | TGG | C242W |     | Non functional | 6.00E−03 | Yes | 7   | 13  | 2.5 |
| 13367 | 244 | GGC | AGC | G244S | Yes | Non functional | 4.00E−02 | Yes | 34  | 70  | 5   |
| 13367 | 244 | GGC | TGC | G244C |     | Non functional | 4.00E−02 | Yes | 30  | 47  | 3   |
| 13367 | 244 | GGC | CGC | G244R |     | Non functional | 4.00E−02 | Yes | 3   | 5   | 2   |
| 13368 | 244 | GGC | GAC | G244D | Yes | Non functional | 4.00E−02 | Yes | 31  | 63  | 5   |
| 13368 | 244 | GGC | GTC | G244V |     | Non functional | 4.00E−02 | Yes | 13  | 24  | 3   |
| 13368 | 244 | GGC | GCC | G244A |     | Non functional | 4.00E−02 | Yes | 9   | 11  | 2.5 |
| 13370 | 245 | GGC | AGC | G245S | Yes | Non functional | 6.00E−06 | Yes | 258 | 436 | 5   |
| 13370 | 245 | GGC | CGC | G245R | Yes | Non functional | 6.00E−06 | Yes | 9   | 18  | 4.5 |
| 13370 | 245 | GGC | TGC | G245C |     | Non functional | 6.00E−06 | Yes | 43  | 83  | 3   |
| 13371 | 245 | GGC | GAC | G245D | Yes | Non functional | 6.00E−06 | Yes | 83  | 153 | 5   |
| 13371 | 245 | GGC | GTC | G245V |     | Non functional | 6.00E−06 | Yes | 1   | 73  | 2.5 |
| 13371 | 245 | GGC | GCC | G245A |     | Non functional | 6.00E−06 | Yes | 7   | 13  | 2.5 |
| 13373 | 246 | ATG | GTG | M246V | Yes | Non functional | 5.00E−02 |     | 25  | 55  | 4   |
| 13373 | 246 | ATG | TTG | M246L | Yes | Non functional | 5.00E−02 |     | 2   | 7   | 3   |
| 13373 | 246 | ATG | CTG | M246L | Yes | Non functional | 5.00E−02 |     | 2   | 1   | 3   |
| 13374 | 246 | ATG | AGG | M246R | Yes | Non functional | 5.00E−02 |     | 10  | 14  | 3.5 |
| 13377 | 247 | AAC | ATC | N247I |     | Non functional | 1.00E−02 | Yes | 1   | 7   | 2   |
| 13377 | 247 | AAC | ACC | N247T |     | Non functional | 1.00E−02 | Yes | 4   | 4   | 2   |
| 13379 | 248 | CGG | TGG | R248W | Yes | Non functional | 7.00E−17 | Yes | 402 | 707 | 5   |
| 13379 | 248 | CGG | GGG | R248G |     | Non functional | 7.00E−17 | Yes | 10  | 23  | 2.5 |
| 13380 | 248 | CGG | CAG | R248Q | Yes | Non functional | 7.00E−17 | Yes | 5   | 865 | 4.5 |

TABLE 3-continued

Supporting evidence for mutations in the Mutation Lookup Table

| | | | | | | | | | | | |
|---|---|---|---|---|---|---|---|---|---|---|---|
| 13380 | 248 | CGG | CTG | R248L | Yes | Non functional | 7.00E−17 | Yes | 2 | 114 | 4.5 |
| 13380 | 248 | CGG | CCG | R248P | | Non functional | 7.00E−17 | Yes | 11 | 18 | 3 |
| 13382 | 249 | AGG | TGG | R249W | Yes | Non functional | 2.00E−03 | Yes | 23 | 40 | 5 |
| 13382 | 249 | AGG | GGG | R249G | | Non functional | 2.00E−03 | Yes | 23 | 47 | 3 |
| 13383 | 249 | AGG | ATG | R249M | Yes | Non functional | 2.00E−03 | Yes | 25 | 66 | 5 |
| 13383 | 249 | AGG | AAG | R249K | | Non functional | 2.00E−03 | Yes | 14 | 27 | 3 |
| 13383 | 249 | AGG | ACG | R249T | | Non functional | 2.00E−03 | Yes | 15 | 30 | 3 |
| 13384 | 249 | AGG | AGT | R249S | Yes | Non functional | 2.00E−03 | Yes | 282 | 389 | 5 |
| 13384 | 249 | AGG | AGC | R249S | Yes | Non functional | 2.00E−03 | Yes | 282 | 40 | 5 |
| 13387 | 250 | CCC | CTC | P250L | | Non functional | 2.00E−03 | Yes | 51 | 10 | 3 |
| 13400 | 255 | ATC | TTC | I255F | | Non functional | | | 15 | 39 | 2 |
| 13407 | 257 | CTG | CAG | L257Q | Yes | Non functional | | | 6 | 16 | 3.5 |
| 13407 | 257 | CTG | CCG | L257P | Yes | Non functional | | | 7 | 14 | 3.5 |
| 13409 | 258 | GAA | TAA | E258* | Yes | | 8.00E−02 | Yes | | 25 | 3.5 |
| 13409 | 258 | GAA | AAA | E258K | | Non functional | 2.00E−03 | Yes | 67 | 14 | 3 |
| 13412 | 259 | GAC | TAC | D259Y | Yes | Non functional | 7.00E−02 | Yes | 14 | 32 | 4 |
| 13413 | 259 | GAC | GTC | D259V | | Non functional | 7.00E−02 | Yes | 12 | 19 | 2 |
| 13774 | 265 | CTG | CCG | L265P | Yes | Non functional | | | 1 | 20 | 3.5 |
| 13776 | 266 | GGA | TGA | G266* | Yes | | 2.00E−02 | Yes | | 29 | 4.5 |
| 13776 | 266 | GGA | AGA | G266R | | Non functional | 2.00E−02 | Yes | 14 | 51 | 3 |
| 13776 | 266 | GGA | CGA | G266R | | Non functional | 2.00E−02 | Yes | 14 | 18 | 3 |
| 13777 | 266 | GGA | GAA | G266E | | Non functional | 2.00E−02 | Yes | 41 | 79 | 3 |
| 13777 | 266 | GGA | GTA | G266V | | Non functional | 2.00E−02 | Yes | 22 | 55 | 3 |
| 13779 | 267 | CGG | TGG | R267W | | Non functional | | | 19 | 31 | 2 |
| 13780 | 267 | CGG | CCG | R267P | | Non functional | | | 12 | 17 | 2 |
| 13789 | 270 | TTT | TGT | F270C | | Non functional | 3.00E−01 | | 15 | 27 | 2 |
| 13791 | 271 | GAG | TAG | E271* | Yes | | 5.00E−02 | | | 17 | 3.5 |
| 13794 | 272 | GTG | ATG | V272M | | Non functional | 1.00E−01 | | 60 | 103 | 2 |
| 13797 | 273 | CGT | TGT | R273C | Yes | Non functional | 4.00E−18 | Yes | 363 | 664 | 5 |
| 13797 | 273 | CGT | AGT | R273S | | Non functional | 4.00E−18 | Yes | 1 | 19 | 2.5 |
| 13797 | 273 | CGT | GGT | R273G | | Non functional | 4.00E−18 | Yes | 8 | 17 | 2.5 |
| 13798 | 273 | CGT | CAT | R273H | Yes | Non functional | 4.00E−18 | Yes | 434 | 812 | 5 |
| 13798 | 273 | CGT | CTT | R273L | Yes | Non functional | 4.00E−18 | Yes | 79 | 142 | 5 |
| 13798 | 273 | CGT | CCT | R273P | | Non functional | 4.00E−18 | Yes | 22 | 37 | 3 |
| 13800 | 274 | GTT | TTT | V274F | Yes | Non functional | 7.00E−01 | | 14 | 33 | 4 |
| 13801 | 274 | GTT | GCT | V274A | | Non functional | 7.00E−01 | | 11 | 18 | 2 |
| 13803 | 275 | TGT | CGT | C275R | | Non functional | 1.00E−02 | Yes | 6 | 15 | 2.5 |
| 13803 | 275 | TGT | AGT | C275S | | Non functional | 1.00E−02 | Yes | 2 | 0 | 2 |
| 13803 | 275 | TGT | GGT | C275G | | Non functional | 1.00E−02 | Yes | 7 | 8 | 2 |
| 13804 | 275 | TGT | TAT | C275Y | | Non functional | 1.00E−02 | Yes | 40 | 75 | 3 |

TABLE 3-continued

Supporting evidence for mutations in the Mutation Lookup Table

| | | | | | | | | | | | |
|---|---|---|---|---|---|---|---|---|---|---|---|
| 13804 | 275 | TGT | TTT | C275F | | Non functional | 1.00E−02 | Yes | 30 | 49 | 3 |
| 13804 | 275 | TGT | TCT | C275S | | Non functional | 1.00E−02 | Yes | 2 | 2 | 2 |
| 13805 | 275 | TGT | TGA | C275* | Yes | Non functional | 1.00E−02 | Yes | | 3 | 4 |
| 13805 | 275 | TGT | TGG | C275W | | Non functional | 1.00E−02 | Yes | 7 | 10 | 2 |
| 13806 | 276 | GCC | CCC | A276P | Yes | Non functional | 7.00E−02 | | 11 | 18 | 4 |
| 13810 | 277 | TGT | TAT | C277Y | | Non functional | 1.00E−01 | | 14 | 27 | 2 |
| 13810 | 277 | TGT | TTT | C277F | | Non functional | 1.00E−01 | | 19 | 51 | 2 |
| 13811 | 277 | TGT | TGA | C277* | Yes | | 1.00E−01 | | | 8 | 3 |
| 13812 | 278 | CCT | ACT | P278T | | Non functional | 1.00E−05 | Yes | 21 | 32 | 3 |
| 13812 | 278 | CCT | TCT | P278S | | Non functional | 1.00E−05 | Yes | 46 | 82 | 3 |
| 13812 | 278 | CCT | GCT | P278A | | Non functional | 1.00E−05 | Yes | 16 | 28 | 3 |
| 13813 | 278 | CCT | CAT | P278H | Yes | Non functional | 1.00E−05 | Yes | 10 | 14 | 4.5 |
| 13813 | 278 | CCT | CTT | P278L | | Non functional | 1.00E−05 | Yes | 51 | 81 | 3 |
| 13813 | 278 | CCT | CGT | P278R | | Non functional | 1.00E−05 | Yes | 24 | 42 | 3 |
| 13816 | 279 | GGG | GAG | G279E | Yes | Non functional | | | 1 | 45 | 3.5 |
| 13818 | 280 | AGA | TGA | R280* | Yes | | 2.00E−01 | | | 9 | 3 |
| 13818 | 280 | AGA | GGA | R280G | | Non functional | 2.00E−01 | | 15 | 41 | 2 |
| 13819 | 280 | AGA | ACA | R280T | Yes | Non functional | 2.00E−01 | | 46 | 91 | 4 |
| 13819 | 280 | AGA | AAA | R280K | | Non functional | 2.00E−01 | | 37 | 70 | 2 |
| 13819 | 280 | AGA | ATA | R280I | | Non functional | 2.00E−01 | | 11 | 24 | 2 |
| 13820 | 280 | AGA | AGT | R280S | Yes | Non functional | 2.00E−01 | | 4 | 19 | 3.5 |
| 13820 | 280 | AGA | AGC | R280S | Yes | Non functional | 2.00E−01 | | 4 | 5 | 3 |
| 13821 | 281 | GAC | AAC | D281N | Yes | Non functional | 4.00E−03 | Yes | 18 | 33 | 5 |
| 13821 | 281 | GAC | TAC | D281Y | Yes | Non functional | 4.00E−03 | Yes | 5 | 11 | 4.5 |
| 13821 | 281 | GAC | CAC | D281H | | Non functional | 4.00E−03 | Yes | 18 | 38 | 3 |
| 13822 | 281 | GAC | GGC | D281G | Yes | Non functional | 4.00E−03 | Yes | 9 | 14 | 4.5 |
| 13822 | 281 | GAC | GTC | D281V | | Non functional | 4.00E−03 | Yes | 2 | 4 | 2 |
| 13822 | 281 | GAC | GCC | D281A | | Non functional | 4.00E−03 | Yes | 2 | 5 | 2 |
| 13823 | 281 | GAC | GAA | D281E | Yes | Non functional | 4.00E−03 | Yes | 9 | 20 | 4.5 |
| 13823 | 281 | GAC | GAG | D281E | Yes | Non functional | 4.00E−03 | Yes | 9 | 24 | 4.5 |
| 13824 | 282 | CGG | GGG | R282G | | Non functional | 2.00E−07 | Yes | 25 | 46 | 3 |
| 13824 | 282 | CGG | TGG | R282W | | Non functional | 2.00E−07 | Yes | 10 | 554 | 2.5 |
| 13825 | 282 | CGG | CCG | R282P | | Non functional | 2.00E−07 | Yes | 13 | 22 | 3 |
| 13825 | 282 | CGG | CAG | R282Q | | | 2.00E−07 | Yes | 19 | 26 | 2 |
| 13828 | 283 | CGC | CAC | R283H | | Non functional | 5.00E−01 | | 11 | 17 | 2 |
| 13828 | 283 | CGC | CCC | R283P | | Non functional | 5.00E−01 | | 21 | 35 | 2 |
| 13833 | 285 | GAG | TAG | E285* | Yes | | 1.00E−01 | | | 21 | 3.5 |
| 13833 | 285 | GAG | AAG | E285K | | Non functional | 1.00E−01 | | 87 | 169 | 2 |
| 13834 | 285 | GAG | GTG | E285V | | Non functional | 1.00E−01 | | 13 | 19 | 2 |
| 13836 | 286 | GAA | TAA | E286* | Yes | | 1.00E−03 | Yes | | 21 | 4.5 |
| 13836 | 286 | GAA | AAA | E286K | | Non functional | 1.00E−03 | Yes | 1 | 83 | 2.5 |

TABLE 3-continued

Supporting evidence for mutations in the Mutation Lookup Table

| | | | | | | | | | | | |
|---|---|---|---|---|---|---|---|---|---|---|---|
| 13836 | 286 | GAA | CAA | E286Q | | | Non functional | 1.00E−03 | Yes | 5 | 15 | 2.5 |
| 13837 | 286 | GAA | GGA | E286G | | | Non functional | 1.00E−03 | Yes | 14 | 19 | 3 |
| 13837 | 286 | GAA | GTA | E286V | | | Non functional | 1.00E−03 | Yes | 6 | 6 | 2 |
| 13837 | 286 | GAA | GCA | E286A | | | Non functional | 1.00E−03 | Yes | 1 | 2 | 2 |
| 13838 | 286 | GAA | GAT | E286D | | | Non functional | 1.00E−03 | Yes | 1 | 3 | 2 |
| 13838 | 286 | GAA | GAC | E286D | | | Non functional | 1.00E−03 | Yes | 1 | 1 | 2 |
| 13839 | 287 | GAG | TAG | E287* | Yes | | | | | | 14 | 3.5 |
| 13842 | 288 | AAT | GAT | N288D | | Yes | | | | 1 | 1 | 2 |
| 13851 | 291 | AAG | TAG | K291* | Yes | | | | | | 7 | 3 |
| 13854 | 292 | AAA | TAA | K292* | Yes | | | | | | 2 | 3 |
| 13860 | 294 | GAG | TAG | E294* | Yes | | | | | | 57 | 3.5 |
| 13872 | 298 | GAG | TAG | E298* | Yes | | | | | | 64 | 3.5 |
| 13893 | 305 | AAG | TAG | K305* | Yes | | | | | | 15 | 3.5 |
| 13896 | 306 | CGA | TGA | R306* | Yes | | Non functional | 9.00E−02 | | 164 | | 4.5 |
| 16900 | 337 | CGC | TGC | R337C | | | Non functional | 9.00E−02 | | 11 | 18 | 2 |

| NtNum | Codon | Change | Protein Change | Stop Codon (3 pts) | Splice Defect (3 pts) | Dominant Negative (2 pts) | Trans-activation (1 pt) | P53 Signature P-Value | P53 signature p value <0.05 (1 pt) | Reported >10x in somatic @ AA level (0.5 pt) | Reported >10x in somatic @ Base level (0.5 pt) | Evidence Score |
|---|---|---|---|---|---|---|---|---|---|---|---|---|
| 11080 | 2-intron | G > A | N/A | | Yes | | | | | | | 3 |
| 11080 | 2-intron | G > C | N/A | | Yes | | | | | | | 3 |
| 11080 | 2-intron | G > T | N/A | | Yes | | | | | | | 3 |
| 11081 | 2-intron | del167 | N/A | | Yes | | | | | | | 3 |
| 11081 | 2-intron | T > A | N/A | | Yes | | | | | | | 3 |
| 11081 | 2-intron | T > C | N/A | | Yes | | | | | | | 3 |
| 11081 | 2-intron | T > G | N/A | | Yes | | | | | | | 3 |
| 11195 | 2-intron | A > C | N/A | | Yes | | | | | | | 3 |
| 11195 | 2-intron | A > G | N/A | | Yes | | | | | | | 3 |
| 11195 | 2-intron | A > T | N/A | | Yes | | | | | | | 3 |
| 11196 | 2-intron | G > A | N/A | | Yes | | | | | | | 3 |
| 11196 | 2-intron | G > C | N/A | | Yes | | | | | | | 3 |
| 11196 | 2-intron | G > T | N/A | | Yes | | | | | | | 3 |
| 11219 | 3-intron | G > A | N/A | | Yes | | | | | | | 3 |
| 11219 | 3-intron | G > C | N/A | | Yes | | | | | | | 3 |
| 11219 | 3-intron | G > T | N/A | | Yes | | | | | | | 3 |
| 11220 | 3-intron | T > A | N/A | | Yes | | | | | | | 3 |
| 11220 | 3-intron | T > C | N/A | | Yes | | | | | | | 3 |
| 11220 | 3-intron | T > G | N/A | | Yes | | | | | | | 3 |
| 11326 | 3-intron | A > C | N/A | | Yes | | | | | | | 3 |
| 11326 | 3-intron | A > G | N/A | | Yes | | | | | | | 3 |
| 11326 | 3-intron | A > T | N/A | | Yes | | | | | | | 3 |
| 11327 | 3-intron | del19 | N/A | | Yes | | | | | | | 3 |
| 11327 | 3-intron | G > A | N/A | | Yes | | | | | | | 3 |
| 11327 | 3-intron | G > C | N/A | | Yes | | | | | | | 3 |
| 11327 | 3-intron | G > T | N/A | | Yes | | | | | | | 3 |
| 11607 | 4-intron | G > A | N/A | | Yes | | | | | | | 3 |
| 11607 | 4-intron | G > C | N/A | | Yes | | | | | | | 3 |
| 11607 | 4-intron | G > T | N/A | | Yes | | | | | | | 3 |
| 11608 | 4-intron | ins1 | N/A | | Yes | | | | | | | 3 |
| 11608 | 4-intron | T > A | N/A | | Yes | | | | | | | 3 |
| 11608 | 4-intron | T > C | N/A | | Yes | | | | | | | 3 |
| 11608 | 4-intron | T > G | N/A | | Yes | | | | | | | 3 |
| 12362 | 4-intron | A > C | N/A | | Yes | | | | | | | 3 |
| 12362 | 4-intron | A > G | N/A | | Yes | | | | | | | 3 |
| 12362 | 4-intron | A > T | N/A | | Yes | | | | | | | 3 |
| 12362 | 4-intron | del1 | N/A | | Yes | | | | | | | 3 |
| 12362 | 4-intron | ins1 | N/A | | Yes | | | | | | | 3 |
| 12363 | 4-intron | del1 | N/A | | Yes | | | | | | | 3 |
| 12363 | 4-intron | G > A | N/A | | Yes | | | | | | | 3 |
| 12363 | 4-intron | G > C | N/A | | Yes | | | | | | | 3 |
| 12363 | 4-intron | G > T | N/A | | Yes | | | | | | | 3 |
| 12548 | 5-intron | G > A | N/A | | Yes | | | | | | | 3 |
| 12548 | 5-intron | G > C | N/A | | Yes | | | | | | | 3 |
| 12548 | 5-intron | G > T | N/A | | Yes | | | | | | | 3 |
| 12549 | 5-intron | T > A | N/A | | Yes | | | | | | | 3 |

TABLE 3-continued

Supporting evidence for mutations in the Mutation Lookup Table

| 12549 | 5-intron | T > C | N/A | Yes | 3 |
|---|---|---|---|---|---|
| 12549 | 5-intron | T > G | N/A | Yes | 3 |
| 12627 | 5-intron | A > C | N/A | Yes | 3 |
| 12627 | 5-intron | A > G | N/A | Yes | 3 |
| 12627 | 5-intron | A > T | N/A | Yes | 3 |
| 12627 | 5-intron | del10 | N/A | Yes | 3 |
| 12628 | 5-intron | del1 | N/A | Yes | 3 |
| 12628 | 5-intron | G > A | N/A | Yes | 3 |
| 12628 | 5-intron | G > C | N/A | Yes | 3 |
| 12628 | 5-intron | G > T | N/A | Yes | 3 |
| 12628 | 5-intron | GG > AA | N/A | Yes | 3 |
| 12742 | 6-intron | del1 | N/A | Yes | 3 |
| 12742 | 6-intron | G > A | N/A | Yes | 3 |
| 12742 | 6-intron | G > C | N/A | Yes | 3 |
| 12742 | 6-intron | G > T | N/A | Yes | 3 |
| 12743 | 6-intron | T > A | N/A | Yes | 3 |
| 12743 | 6-intron | T > C | N/A | Yes | 3 |
| 12743 | 6-intron | T > G | N/A | Yes | 3 |
| 13308 | 6-intron | A > C | N/A | Yes | 3 |
| 13308 | 6-intron | A > G | N/A | Yes | 3 |
| 13308 | 6-intron | A > T | N/A | Yes | 3 |
| 13308 | 6-intron | del11 | N/A | Yes | 3 |
| 13309 | 6-intron | G > A | N/A | Yes | 3 |
| 13309 | 6-intron | G > C | N/A | Yes | 3 |
| 13309 | 6-intron | G > T | N/A | Yes | 3 |
| 13420 | 7-intron | del137 | N/A | Yes | 3 |
| 13420 | 7-intron | del342 (del intron7) | N/A | Yes | 3 |
| 13420 | 7-intron | G > A | N/A | Yes | 3 |
| 13420 | 7-intron | G > C | N/A | Yes | 3 |
| 13420 | 7-intron | G > T | N/A | Yes | 3 |
| 13421 | 7-intron | del10 | N/A | Yes | 3 |
| 13421 | 7-intron | T > A | N/A | Yes | 3 |
| 13421 | 7-intron | T > C | N/A | Yes | 3 |
| 13421 | 7-intron | T > G | N/A | Yes | 3 |
| 13759 | 7-intron | G > A | N/A | Yes | 3 |
| 13761 | 7-intron | A > C | N/A | Yes | 3 |
| 13761 | 7-intron | A > G | N/A | Yes | 3 |
| 13761 | 7-intron | A > T | N/A | Yes | 3 |
| 13762 | 7-intron | G > A | N/A | Yes | 3 |
| 13762 | 7-intron | G > C | N/A | Yes | 3 |
| 13762 | 7-intron | G > T | N/A | Yes | 3 |
| 13762 | 7-intron | ins3 | N/A | Yes | 3 |

"del" denotes deletion of the number of basepairs;
"ins" denotes insertion of the number of baspairs.

Example 2

A Phase II study was conducted with WEE1-1 Inhibitor combined with carboplatin in patients with p53 mutated epithelial ovarian cancer that show early relapse (<3 months) or progression during standard first line treatment with carboplatin-paclitaxel combination therapy. Patients were enrolled based on the tumor's TP53 gene sequence as determined in the AmpliChip p53 assay.

AmpliChip p53 test reagents are used to amplify products encompassing the coding regions of the p53 gene in two reactions (A and B) for all samples including a reference wildtype DNA. Exons 2, 5, 8, and 10; exon 4 upstream sequence; and internal control are in the Primer Mix A. Primer Mix B is designed and contained primers for exons 3, 6, 7, 9, and 11; exon 4 downstream sequence; and internal control. After thermal cycling, the products from Primer Mixes A and B are combined. The products generated from the A and B reactions are cleaved by a mix containing DNase I. Fragmentation is performed by recombinant DNase I to generate small DNA fragments of an average size of 50-100 nucleotides. The alkaline phosphatase in the Working Fragmentation Mix destroys the residual dNTPs from the amplification reactions. The fragmented DNA amplicons are subsequently labeled with biotin at their 3' termini by the action of terminal transferase, using AmpliChip TdT Labeling Reagent as substrate. The biotin-labeled p53 target DNA fragments are added to the hybridization buffer containing the AmpliChip Oligonucleotide Solution which functions as a hybridization control. The mixture is hybridized to the oligonucleotides located on the AmpliChip p53 Microarray using the Affymetrix GeneChip Fluidics Station 450Dx and an AmpliChip p53 specific protocol. The hybridized AmpliChip p53 Microarray is washed and stained with a streptavidin-conjugated fluorescent dye.

Design of the AmpliChip p53 Microarray

The microarray consists of a square grid of 228,484 probes, with sides that are 11 micron each. Each probe contains multiple copies of a specific oligonucleotide sequence. A single probe set for an interrogating base position includes five probes, one probe to hybridize to the wild type, three probes to detect three possible single base pair mutations, and one probe to detect single deletion. There are at least 24 probe sets for each nucleotide position, including both sense and antisense probe sequences. A total of 1300 nucleotide positions of coding regions of exons 2-11 are tiled on AmpliChip p53. AmpliChip p53 Microarrays are manufactured using technology that combines photolithographic methods and combinatorial chemistry. Over 220,000 different oligonucleotide probes are synthesized on a glass surface to analyze both sense and antisense strands of an amplified target DNA specimen. Within the 11×11 µm² probe microarray, each probe type is located in a specific area called a probe cell, which contains approximately 106 copies of a given probe. Probe microarrays are manufactured by light-directed combinatorial chemistry in a series of cycles. The glass substrates are coated with linkers containing photolabile protecting groups. A mask is then applied that exposes selected portions of the probe microarray. Illumination removes the photolabile protecting groups enabling selective nucleoside phosphoramidite addition only at the previously exposed sites. Next, a different mask is applied and the cycle of illumination and chemical coupling is performed again. By repeating this cycle, a specific set of oligonucleotide probes is synthesized, with each probe type in a known location. The completed probe microarrays are packaged into cartridges compatible with the GeneChip Fluidics Station 450Dx. After staining, the AmpliChip p53 Microarray is scanned by an Affymetrix GeneChip Scanner 3000Dx using a laser that excites the fluorescent label bound to the hybridized p53 target DNA fragments. The amount of emitted light is proportional to bound target DNA at each location on the probe microarray.

Data Analysis of Microarray Signals

The p53 mutation status is determined by a p53 mutation detection algorithm, which is designed to detect single base pair substitutions and single base pair deletions of a sample in a background of wild type p53 DNA probe intensities. The algorithm first reads the probe intensities generated by the GeneChip Operating Software, Version 1.1 provided by Affymetrix. Based on the raw data, the algorithm performs an initial exon quality test to detect distinct problems in each PCR product. If an exon fails the initial quality test, the exon failure is reported and no further analysis is made. If an exon passes the test, the probe intensities are normalized by using quantile normalization in order to correct array-to-array variability.

The quality of each probe set is then examined to eliminate unreliable probe set data for further computation. Using probes sets that passed the quality tests, the algorithm makes a tentative call for each base position. Possible base calls for each nucleotide position are wild type, single base substitution, single base deletion, or no call (unable to make a call). In the case of a single base substitution, the algorithm identifies the mutated base (e.g., G® A). After the tentative calls are made, the reliability of each base call is reexamined by the algorithm to fine tune the calls using various parameters calculated from the neighboring base positions. Each exon quality is also reexamined based on the final base calls. If there are too many no calls and/or mutation calls in one exon, the data is considered as "noisy," and the exon fails the quality test. If an exon fails, the exon failure is reported, and no calls are reported for that exon.

Tumor Response Evaluation

Patients were evaluable for response to study treatment if at least one follow-up examination was performed at the end of the second treatment cycle (at least a six-week period). Tumor response was assessed either in measurable or evaluable tumor lesions according to the RECIST 1.0 criteria (Appendix IV). In the case of stable disease, a confirmation was necessary within 6 to 8 weeks of initial assessment. In case of stable disease at the end of treatment or in case of discontinuation for unacceptable adverse experiences evaluation took place every 2 months and CA-125 (cancer antigen) was determined. In case of a CA-125 increase a CT scan was performed. In patients for whom CA-125 is not a good marker, a CT-scan was performed every 2 months, until disease progression. Patients without radiologically measurable disease had elevated CA-125 prior to start and were evaluated based on CA-125 levels. CT-scans were also performed in these patients. According to the Gynecologic Cancer Intergroup (GCIG) CA-125 response criteria, progressive disease after a complete response to primary therapy is defined as follows: the date of first elevation of CA-125 to two-fold the upper limit of normal (ULN) (documented on two occasions at least a week apart). For those with persistently elevated CA-125 levels, progression of disease is defined as the first date of CA-125≥2× the nadir value documented on two occasions no less than a week apart. The ULN for CA-125 at the NKI is 35 U/mL. However, in this study for patients with CA-125 nadir≤10 U/mL, a confirmed value of ≥20 U/mL served as an early signal of CA-125 progression, and for patients with nadir more than 10 U/mL, a value ≥2× nadir. The definition of disease progression included both the standard RECIST criterion and the CA-125 criterion as defined above, whichever occurs first. Response regarding CA-125 is defined standards as 50% reduction during treatment of CA-125.

The following table summarizes the p53 amino acid mutation information for responders in the above clinical trial.

TABLE 4

| Patient Number | PCR | Amino Acid/Gene mutation | Mutation listed in Table 3 | Responder |
| --- | --- | --- | --- | --- |
| 1003 | Exon 7 | C238F | Yes | Yes |
| 1008 | Exon 7 | R248W | Yes | Yes |
| 1010 | Exon 8 | E298 stop codon | Yes | Yes |
| 1011 | Exon 8 | R273L | Yes | Yes |
| 1015 | Exon 5 | V157 frameshift | Yes | Yes |

Example 4

In a randomized, Phase II study evaluating WEE1-1 in combination with paclitaxel and carboplatin versus paclitaxel and carboplatin alone in adult patients with platinum sensitive p53 mutant ovarian cancer, patient enrollment was based on the presence of one or more mutations in Table 3. If the specimen has no mutations in the TP53 gene, or if it contains a mutation not listed on the Mutation Lookup Table 3, the patient will not be eligible for the study. If the specimen had at least one mutation that is listed in the Mutation Lookup Table 3, the patient was eligible for enrollment in the study.

Analysis of patient tumor tissue samples using the AmpliChip p53 assay was performed by Canis Life Sciences (Phoenix, Ariz.). The AmpliChip p53 assay characterized each specimen as 'Mutation Not Detected,' 'Mutation Detected' or 'Test Invalid'. A base change to a synonymous codon is treated as a Mutation Not Detected call, since it does not alter the amino acid. There are seven single-nucleotide polymorphisms reported in the IARC database R15 (2010 release) within the tiled nucleotide positions of AmpliChip 53. While three do not result in amino acid changes (codons 34, 36 and 213), four others result in the following amino acid changes: P47S, P72R, V217M and G360A. These are all treated as Mutation Not Detected, and are not reported. If at least one mutation is detected, the sample is called "Mutation Detected" and the nucleotide change detected is reported, along with the corresponding amino acid change in the p53 protein. If no base changes are detected and the test is valid, the sample is called "Mutation Not Detected."

What is claimed:

1. A method of treating cancer in a patient having one or more TP53 gene mutations, the method comprising administering to the patient a therapeutically effective amount of a WEE1 inhibitor and optionally one or more additional anti-cancer agents, wherein the patient is predicted to be responsive to treatment with the WEE1 inhibitor, the process of prediction comprising:
   1) identifying all TP53 gene mutations in a patient tumor tissue sample comprising cancer cells;
   2) calculating an evidence score based on an additive point value for each identified TP53 gene mutation; and
   3) predicting the patient as responsive to treatment with the WEE1 inhibitor when the evidence score is equal to or greater than 2.0;
wherein the evidence score for a TP53 gene mutation of step (2) is calculated by (a) assigning to each type of TP53 gene mutation a point value related to a likelihood that the mutation results in a loss of function of p53 protein; and (b) adding together the TP53 gene mutation point values to afford the evidence score.

2. The method of claim 1, wherein the process of predicting the patient as responsive to respond to treatment with the WEE1 inhibitor further comprises calculating a point value for each type of TP53 gene mutation patient.

3. The method of claim 1, wherein the at least one TP53 gene mutation is selected from the group consisting of E2, K120, V143M, A159D, C176F, R196P, C229, C242S, R249S, C275G, R282G, E3, C124, V143A, A161D, C176Y, V197G, Y234H, C242, P250L, C275Y, R282W, Q5, Y126, Q144, Y163N, C176S, E198, Y234C, C242W, I255F, C275F, R282P, S6, S127P, L145Q, Y163H, C176, G199, Y234, G244S, L257Q, C275S, R282Q, E11, S127T, L145P, Y163D, C176W, G199E, Y236D, G244C, L257P, C275, R283H, Q16, S127F, W146, Y163C, P177S, L201, Y236H, G244R, E258, C275W, R283P, E17, S127Y, D148, Y163S, P177H, E204, Y236N, G244D, E258K, A276P, E285, S20, S127C, P151T, Y163, P177R, Y205D, Y236C, G244V, D259Y, C277Y, E285K, W23, K132, P151S, K164, H179N, Y205S, Y236S, G244A, D259V, C277F, E285V, K24, K132Q, P151A, K164E, H179Y, Y205C, Y236, G245S, N263, C277, E286, E28, K132E, P151R, Q165, H179R, Y205, M237I, G245R, L265P, P278T, E286K, L35, K132R, P151H, S166, H179L, L206, C238R, G245C, G266, P278S, E286Q, Q38, K132M, P152S, Q167, H179Q, R209, C238Y, G245D, G266R, P278A, E286G, L43, K132T, P152L, H168Y, H179, R213, C238F, G245V, G266E, P278H, E286V, E51, K132N, G154V, H168R, E180, R213Q, C238, G245A, G266V, P278L, E286A, Q52, M133K, T155P, H168P, C182, R213L, N239D, M246V, R267W, P278R, E286D, W53, C135R, T155N, H168L, S183, H214R, N239S, M246L, R267P, G279E, E287, E56, C135S, R156P, E171, S183, S2151, N239, M246R, F270C, R280, N288D, E62, C135G, V157F, V173M, Q192, V216M, S240G, N247I, E271, R280G, K291, R65, C135Y, V157L, V173L, H193Y, V216L, S241T, N247T, V272M, R280T, K292, E68, C135F, V157D, V173G, H193D, V216E, S241A, R248W, R273C, R280K, E294, W91, C135S, V157G, V173E, H193N, V216G, S241P, R248G, R273S, R280I, E298, S94, C135, V157A, R175G, H193L, Y220N, S241F, R248Q, R273G, R280S, K305, Q100, C135W, R158G, R175C, H193P, Y220H, S241C, R248L, R273H, D281N, R306, K101, Q136, R158S, R175H, H193R, Y220D, S241Y, R248P, R273L, D281Y, R337C, Y103, A138P, R158P, R175L, L194F, Y220C, C242S, R249W, R273P, D281H, Q104, A138G, R158H, R175P, L194R, Y220S, C242R, R249G, V274F, D281G, Y107, K139, R158L, C176R, I195F, Y220, C242G, R249M, V274A, D281V, R110L, C141Y, A159P, C176S, I195T, E221, C242Y, R249K, C275R, D281A, L114, C141, A159V, C176G, R196, E224, C242F, R249T, C275S, D281E, at least one basepair insertion or deletion in the TP53 gene that causes a frameshift in encoding a p53 protein resulting in loss of function, and a combination thereof in the cancer cells.

4. The method of claim 3, wherein the patient has at least one TP53 gene mutation resulting in an amino acid change selected from the group consisting of C238F, R248W, R273L, a stop codon at the codon encoding E298 in the p53 protein, and a deletion of a basepair in the codon encoding V157 in the p53 protein.

5. The method of claim 1, wherein the at least one TP53 gene mutation results in a loss of function of p53 protein.

6. The method of claim 1, wherein the WEE1 inhibitor is

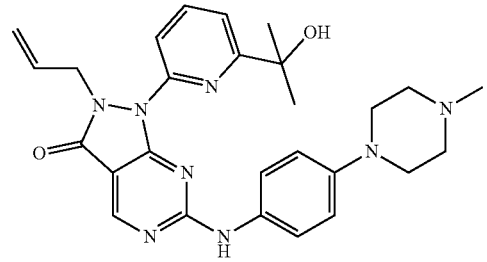 [SMILES: C=CCn1c(=O)c2cnc(Nc3ccc(N4CCN(C)CC4)cc3)nc2n1-c1cccc(C(C)(C)O)n1]

or a pharmaceutically acceptable salt thereof.

7. The method of claim 1, wherein the WEE1 inhibitor is

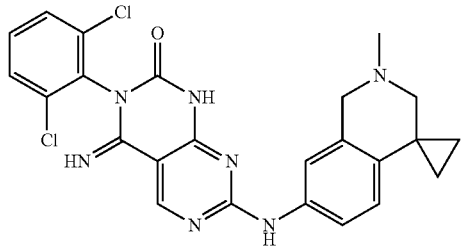 [SMILES: CN1Cc2cc(Nc3ncc4c(=N)n(-c5c(Cl)cccc5Cl)c(=O)[nH]c4n3)ccc2C2(CC2)C1]

or a pharmaceutically acceptable salt thereof.

8. The method of claim 1, wherein the cancer is selected from the group consisting of ovarian cancer, melanoma, lung cancer, colorectal cancer, colon cancer, rectum cancer, prostate cancer, and breast cancer.

9. The method of claim 8, wherein the cancer is ovarian cancer.

10. The method of claim 8, wherein the cancer is lung cancer.

11. The method of claim 1, wherein the additional anti-cancer agent is selected from the group consisting of: 5-FU, carboplatin, paclitaxel, doxorubicin, etoposide, gemcitabine, irinotecan, mitomycin, temozolomide, topotecan, and a combination thereof.

12. The method of claim 11, wherein the additional anti-cancer agent is carboplatin.

13. The method of claim 11, wherein the additional anti-cancer agents are carboplatin and paclitaxel.

14. The method of claim 1, wherein the one or more additional anti-cancer agents are administered subsequent to administering the WEE1 inhibitor to the patient.

15. The method of claim 14, wherein the method does not comprise administering the one or more additional anti-cancer agents prior to administering the WEE1 inhibitor.

16. The method of claim 1, wherein the point value assigned for each type of TP53 gene mutation is selected from:
  (a) a stop codon mutation (truncated protein) prior to codon 306 has a point value of 3;
  (b) a splice site mutation between codons 97 and 375 has a point value of 3;
  (c) a frameshift mutation has a point value of 3;
  (d) a dominant negative mutation has a point value of 2;
  (e) a P53 signature score p-value <0.05 vs. wild type (WT) has a point value of 1;
  (f) a transactivation loss-of-function mutation has a point value of 1;
  (g) mutations reported over ten times in at nucleotide level in International Agency for Research on Cancer (IARC) TP53 database has a point value of 0.5; and,
  (h) mutations reported over ten times in somatic tissue at amino acid level in IARC TP53 database has a point value of 0.5.

* * * * *